(12) United States Patent
Fujita et al.

(10) Patent No.: US 10,845,333 B2
(45) Date of Patent: Nov. 24, 2020

(54) DNA DETECTION METHOD

(71) Applicants: The Foundation for the Promotion of Industrial Science, Tokyo (JP); Neuroindx, Inc., Signal Hill, CA (US); Centre National De La Recherche Scientifique, Paris (FR)

(72) Inventors: Hiroyuki Fujita, Tokyo (JP); Stanislav L. Karsten, Signal Hill, CA (US); Dominique Collard, Tokyo (JP); Momoko Kumemura, Tokyo (JP)

(73) Assignees: The Foundation for the Promotion of Industrial Science, Tokyo (JP); Neuroindx, Inc., Torrance, CA (US); Centre National de la Recherche Scientifique (CNRS), Paris (FR)

( * ) Notice: Subject to any disclaimer, the term of this patent is extended or adjusted under 35 U.S.C. 154(b) by 650 days.

(21) Appl. No.: 15/031,849

(22) PCT Filed: Oct. 24, 2014

(86) PCT No.: PCT/JP2014/078298
§ 371 (c)(1),
(2) Date: Jan. 6, 2017

(87) PCT Pub. No.: WO2015/060417
PCT Pub. Date: Apr. 30, 2015

(65) Prior Publication Data
US 2017/0168012 A1 Jun. 15, 2017

(30) Foreign Application Priority Data
Oct. 25, 2013 (JP) .................................. 2013-221803

(51) Int. Cl.
*G01N 27/447* (2006.01)
*G01N 27/327* (2006.01)
(Continued)

(52) U.S. Cl.
CPC ....... *G01N 27/4473* (2013.01); *C12Q 1/6844* (2013.01); *G01N 27/3275* (2013.01);
(Continued)

(58) Field of Classification Search
CPC .......... G01N 27/4473; G01N 27/3275; G01N 27/3278; G01N 27/44791; C12Q 1/6844; B01L 3/5027
(Continued)

(56) References Cited

U.S. PATENT DOCUMENTS

2005/0123937 A1* 6/2005 Thorp .................. B82Y 15/00
435/6.12
2008/0003142 A1* 1/2008 Link ..................... B01F 3/0807
422/82.08
(Continued)

FOREIGN PATENT DOCUMENTS

JP 2005520130 A 7/2005
JP 2007512810 A 5/2007
(Continued)

OTHER PUBLICATIONS

Yamahata, C. et al. (2008). Silicon Nanotweezers with Subnanometer Resolution for the Micromanipulation of Biomolecules. J Microelectromechanical Sys. 17(3). 623-631. (Year: 2008).*
(Continued)

*Primary Examiner* — Benjamin R Whatley
*Assistant Examiner* — Jacqueline Brazin
(74) *Attorney, Agent, or Firm* — Banner & Witcoff, Ltd.

(57) ABSTRACT

An object is to make a bridge of DNA expanding between a pair of electrodes, and to characterize the bridge of DNA, to thereby detect DNA easily and surely without employing any marker or labeling substances, such as fluorescent reagents. A method of detecting DNA using a detection device with at least a couple of electrodes, the method
(Continued)

comprising immobilizing a primer on the electrodes; making a bridge of the DNA expanded between the electrodes, by immersing the electrodes in a solution including circular templates of single stranded DNA, annealing the circular templates, and generating single stranded DNA product utilizing RCA (Rolling Circle Amplification), with impressing a designated voltage between the electrodes; and characterizing the bridge of DNA which includes multiple single stranded DNA molecules between the electrodes.

13 Claims, 16 Drawing Sheets

(51) Int. Cl.
  *C12Q 1/68* (2018.01)
  *G01N 33/487* (2006.01)
  *C12Q 1/6844* (2018.01)
  *B01L 3/00* (2006.01)
(52) U.S. Cl.
  CPC ... *G01N 27/3278* (2013.01); *G01N 27/44791* (2013.01); *G01N 33/48721* (2013.01); *B01L 3/5027* (2013.01)
(58) Field of Classification Search
  USPC .......................................................... 436/94
  See application file for complete search history.

(56) References Cited

U.S. PATENT DOCUMENTS

| | | | |
|---|---|---|---|
| 2014/0002111 A1* | 1/2014 | Potyrailo | H05K 1/16 324/655 |
| 2014/0224673 A1* | 8/2014 | Alocilja | C12Q 1/6811 205/780.5 |

FOREIGN PATENT DOCUMENTS

| | | |
|---|---|---|
| JP | 2008501122 A | 1/2008 |
| JP | 2013013375 A | 1/2013 |

OTHER PUBLICATIONS

Braun, E. et al., "DNA-templated assembly and electrode attachment of a conducting silver wire", Nature, Feb. 19, 1998, vol. 391, pp. 775-778.
Kumemura, M. et al., "Direct Bio-Mechanical Sensing of Enzymatic Reaction on Dna by Silicon Nanotweezers", 2010 IEEE 23rd International Conference on Micro Electra Mechanical Systems (MEMS), 2010, pp. 915-918.
Kumemura, M. et al., "Single-DNA-molecule trapping with silicon nanotweezers using pulsed dielectrophoresis", Apr. 28, 2011, Journal of Micromechanics and Microengineering, Institute of Physics Publishing, Bristol, GB, vol. 21, No. 5, pp. 1-6.
Lafitte, N. et al., "Closed-loop control of silicon nanotweezers for improvement of sensitivity to mechanical stiffness measurement and bio-sensing on DNA molecules", 2013 IEEE/RSJ International Conference on Intelligent Robots and Systems, IEEE, Nov. 3, 2013, pp. 1022-1027.
Lafitte, N. et al., "Real-time sensing of molecule binding on DNA with silicon nanotweezers", Proc. MicroTAS 2011, pp. 389-391.
Sato, K. et al., "Microbead-based rolling circle amplification in a microchip for sensitive DNA detection", Lab on a Chip, 2010, vol. 10, No. 10, pp. 1262-1266.
Yamahata, C, et al., "Electrical and Mechanical Characteristics of DNA Bundles Revealed by Silicon Nanotweezers", Solid-State Sensors, Actuators and Microsystems Conference, 2007, pp. 395-398.
Yamahata, C. et al., "Silicon Nanotweezers with Subnanometer Resolution for the Micromanipulation of Biomolecules", Journal of Microelectromechanical Systems, Jun. 2008, vol. 17, No. 3, pp. 623-631.

\* cited by examiner

FIGURE 6A
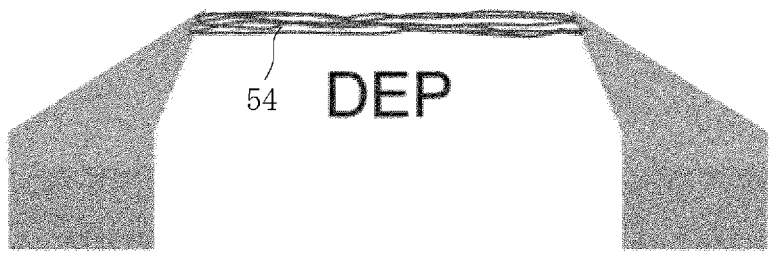
FIGURE 6B     FIGURE 6C     FIGURE 6D
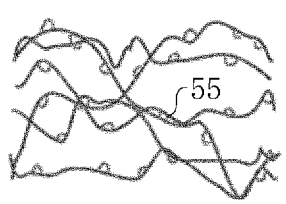 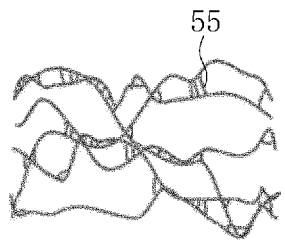 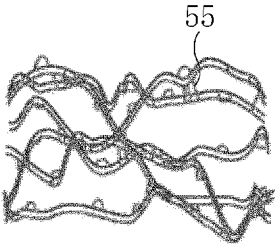
ssDNA     ssDNA     dsDNA
intrastrand   interstrand   both
FIGURE 7
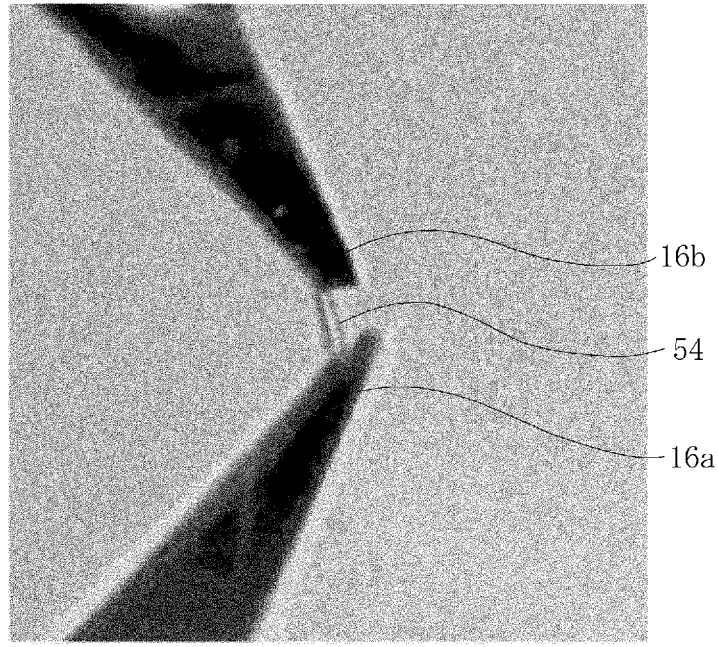

FIGURE 13A   FIGURE 13B   FIGURE 13C
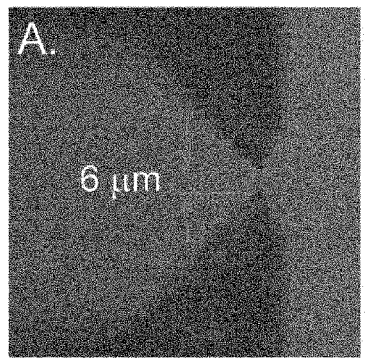 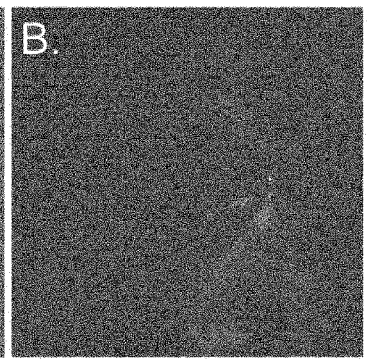 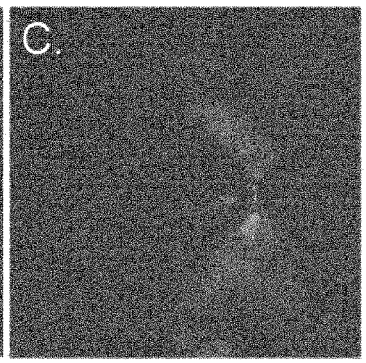
FIGURE 14
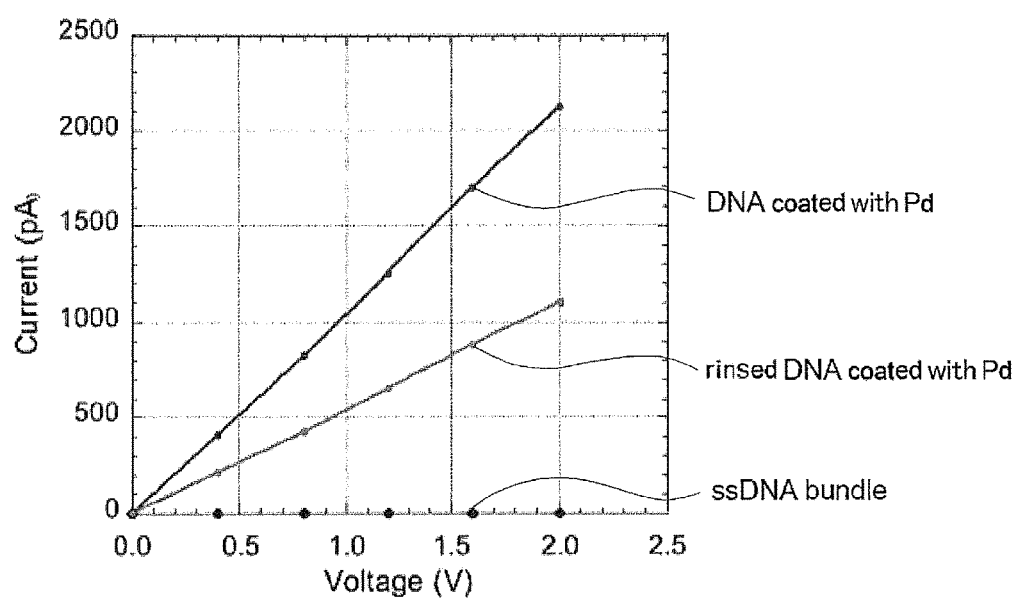

DNA DETECTION METHOD

TECHNICAL FIELD

The present invention relates to a method of detecting DNA.

BACKGROUND ART

From viewpoints of biodefense, medical diagnostics, food safety, environmental monitoring etc., an inexpensive and robust method of detecting DNA has been long in need. Then, methods of detecting DNA using nano-tweezers produced by technology of MEMS (Micro-Electro-Mechanical System) have been proposed (see, for example, Non-Patent Documents 1 and 2).

CITATION LIST

Non-Patent Document 1: M. Kumemura, D. Collard, S. Yoshizawa, D. Fourmy, N. Lafitte, S. Takeuchi, T. Fujii, L. Jalabert, and H. Fujita, "Direct bio-mechanical sensing of enzymatic reaction on DNA by silicon nanotweezers," Proc. IEEE MEMS '10, pp. 915-918, 2010

Non-Patent Document 2: N. Lafitte, M. Kumemura, L. Jalabert, D. Collard, and H. Fujita, "Real-time sensing of molecule binding on DNA with silicon nanotweezers," Proc. MicroTAS 2011, 389-391

SUMMARY OF INVENTION

Problems to be Solved by Invention

However, in the aforementioned conventional methods, DNA included in samples has to be amplified beforehand. And it is difficult to capture and detect very short DNA, for example, about several [nm]-dozen [nm] in length, since there are limits to miniaturization of nano-tweezers.

An object of the present invention is to solve the above-mentioned problems in the conventional techniques and to provide a method of detecting DNA, in which a bridge of DNA expanded between a pair of electrodes is made, and the bridge of DNA is characterized, thereby DNA is easily and surely detected without employing any marker or labeling substances, such as fluorescent reagents.

Solution to Problems

Accordingly, the present invention provides a method of detecting DNA using a detection device with at least a couple of electrodes, the method comprising immobilizing a primer on the electrodes; making a bridge of the DNA expanded between the electrodes, by immersing the electrodes in a solution including circular templates of single stranded DNA, annealing the circular templates, and generating single stranded DNA product utilizing RCA (Rolling Circle Amplification), with impressing a designated voltage between the electrodes; and characterizing the bridge of DNA which includes multiple single stranded DNA molecules between the electrodes.

In another method of detecting DNA of the present invention, at least a part of the electrodes is coated with gold.

In yet another method of detecting DNA of the present invention, making the bridge of DNA expanded between the electrodes is processed isothermally.

In yet another method of detecting DNA of the present invention, characterizing the bridge of DNA is based on a resonance frequency of the bridge of DNA between the electrodes.

In yet another method of detecting DNA of the present invention, a gap between the electrodes is varied at designated frequencies.

In yet another method of detecting DNA of the present invention, the DNA of the bridge between the electrodes is in a bundle.

In yet another method of detecting DNA of the present invention, the DNA of the bridge between the electrodes is in a bundle including double stranded DNA molecules.

In yet another method of detecting DNA of the present invention, characterizing the bridge of DNA is based on an electrical conductance of the bridge of DNA between the electrodes.

In yet another method of detecting DNA of the present invention, characterizing the bridge of DNA is made on real time measurement of the bridge of DNA between the electrodes.

In yet another method of detecting DNA of the present invention, immobilizing different primers on the opposite electrodes so that a single stranded complementary DNA is generated.

In yet another method of detecting DNA of the present invention, immobilizing different primers on multiple couples of electrodes so that each of plural DNA is characterized.

The present invention also provides another method of detecting DNA using a detection device with at least a couple of electrodes, the method comprising immobilizing a primer on the electrodes; making a bridge of the DNA expanded between the electrodes, by immersing the electrodes in a solution including circular templates of single stranded DNA, annealing the circular templates, and generating single stranded DNA product utilizing RCA, with impressing a designated voltage between the electrodes; coating the bridge of the DNA with conductive nanoparticles; and verifying existence of the bridge of DNA between the electrodes.

In yet another method of detecting DNA of the present invention, immobilizing different primers on multiple couples of electrodes so that existence of plural DNA is verified.

Effects of Invention

According to the present invention, in the method of detecting DNA, a bridge of DNA expanded between a couple of electrodes of a detection device is made and the bridge of DNA is characterized. Thereby, DNA is easily and surely detected without employing any marker or labeling substances, such as fluorescent reagents.

BRIEF DESCRIPTION OF DRAWINGS

FIG. 6 is a set of views showing a DNA bridging between the tips of arm members of the nano-tweezers according to the first embodiment of the present invention.

FIG. 7 is a microscopic photo showing the DNA bridging between the tips of arm members of the nano-tweezers according to the first embodiment of the present invention.

FIG. 13 is a set of microscopic photos showing the state where the DNA bridging between the tips of arm members of the nano-tweezers is coated with gold nanoparticles according to the second embodiment of the present invention.

FIG. 14 is a graph showing an electric conductivity of the DNA bridging between the tips of arm members of the nano-tweezers coated with palladium nanoparticles according to the second embodiment of the present invention.

DESCRIPTION OF EMBODIMENTS

An embodiment of the present invention will next be described in detail with reference to the drawings.

Figure 1:
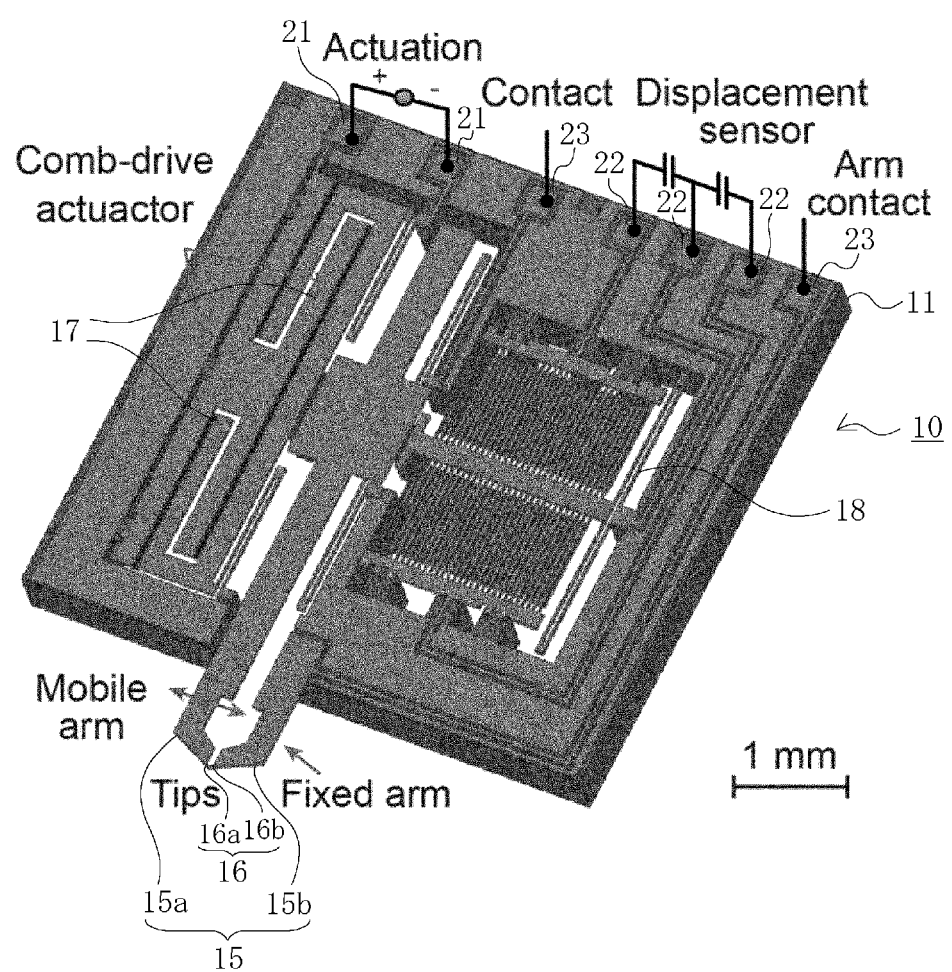
FIG. 1 is a perspective view showing a nano-tweezers according to a first embodiment of the present invention.
Figure 2A:
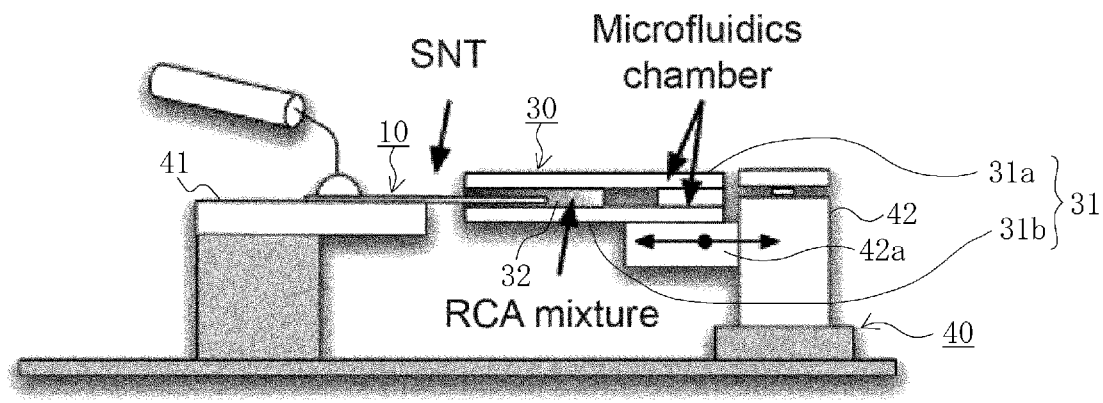
FIG. 2 is a set of views showing a method for immersing tips of arm members of the nano-tweezers in solution according to the first embodiment of the present invention.
Figure 2B:
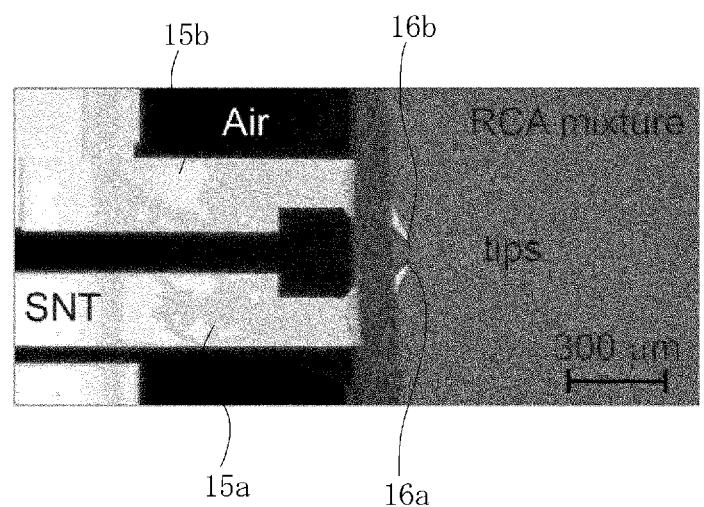
Figure 3:
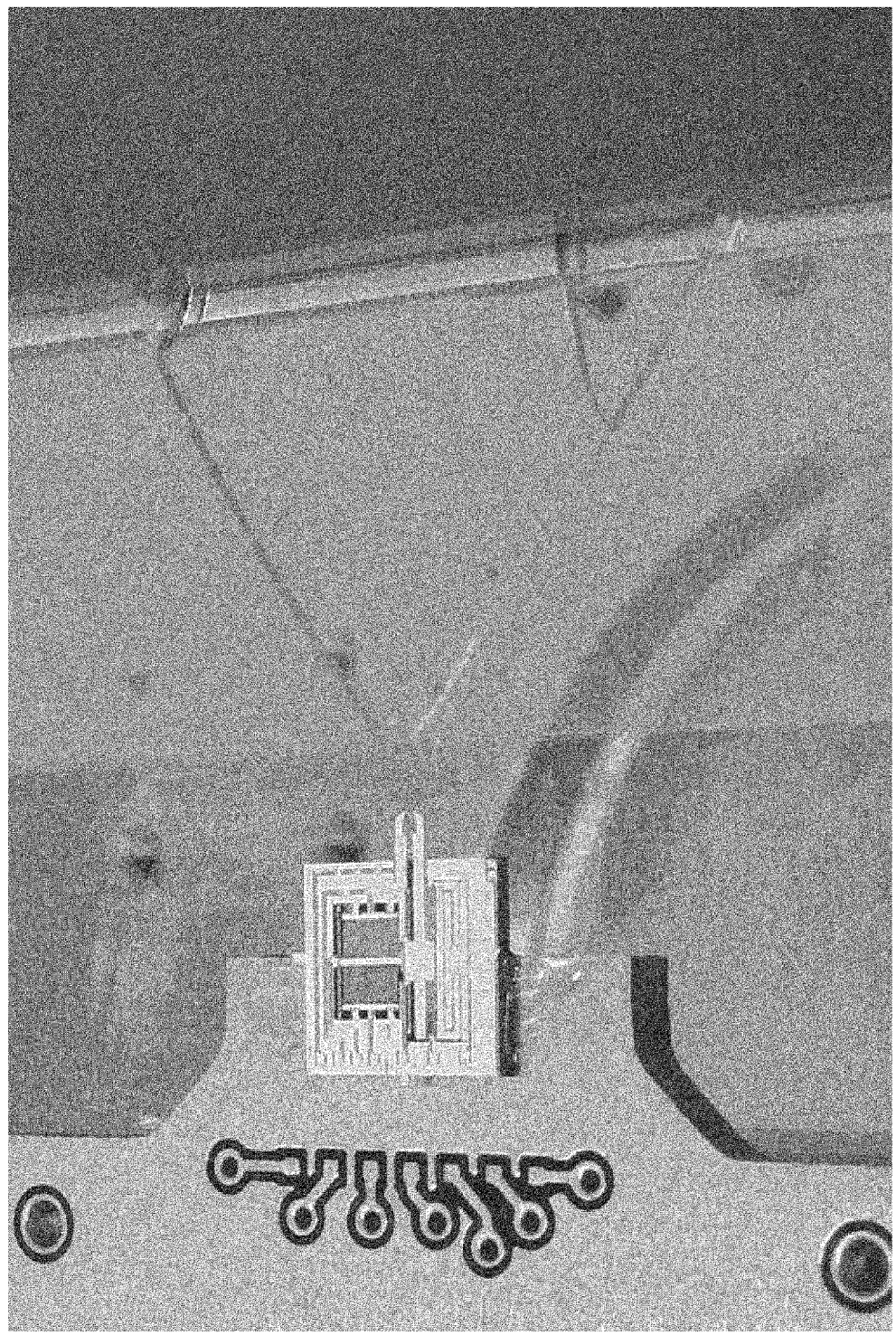
FIG. 3 is a photograph showing the method for immersing the tips of arm members of the nano-tweezers in solution according to the first embodiment of the present invention.

FIG. 1 is a perspective view showing a nano-tweezers according to the first embodiment of the present invention. FIG. 2 is a set of views showing a method for immersing tips of arm members of the nano-tweezers in solution according to the first embodiment of the present invention. FIG. 3 is a photograph showing the method for immersing the tips of arm members of the nano-tweezers in solution according to the first embodiment of the present invention. In FIG. 2, (a) shows a schematic side view and (b) shows a microphotographic top view.

In the respective figures, a reference numeral 10 designates a nano-tweezers, as a detection device employed in the present embodiment, which is a device produced from a silicon substrate by MEMS technology and has a structure similar to the nano-tweezers shown in Non-Patent Documents 1 and 2.

The nano-tweezers 10 includes a main body 11, with a form of plate in a rectangular plane shape, and a pair of arm members 15 protruding in parallel each other from a side of the main body 11. The arm members 15 consist of a moving arm 15a and a fixed arm 15b, the former of which is attached to the main body 11 in a movable or displaceable manner and the latter of which is attached to the main body 11 in an immovable manner. The moving arm 15a and the fixed arm 15b are configured in side by side on a plane parallel to the surface of the main body 11, and the moving arm 15a moves on the plane parallel to the surface of the main body 11.

A moving tip part 16a in a sharp-pointed shape is formed at the tip of the moving arm 15a, and a fixed tip part 16b in a sharp-pointed shape is formed at the tip of the fixed arm 15b. The moving tip part 16a and the fixed tip part 16b are opposing each other. The moving tip part 16a and the fixed tip part 16b will be described as tip parts 16 when it would be better to explain them altogether. The tip parts 16 function as electrodes and designated AC voltage is impressed between them. At least a part of the surface of the tip parts 16 is desirably coated with gold.

The main body 11 includes a comb-drive actuator 17 for displacing the moving arm 15a. The comb-drive actuator 17 is a linear actuator utilizing an electrostatic force acting between non graphically illustrated conductive com teeth, and can displace the moving arm 15a in a direction orthogonal to its major axis, as shown by a two-directional arrow in FIG. 1, to adjust a gap between the moving arm 15a and the fixed arm 15b. Thereby, a gap between the tip parts 16, that is, between the moving tip part 16a and the fixed tip part 16b, can be varied.

The main body 11 also includes a displacement sensor 18 for measuring an amount of displacement of the moving arm 15a. The displacement sensor 18 is a capacitive sensor detecting capacitance variation, and can measure displacement of the moving arm 15a. Thereby, a gap and a gap variation between the tip parts 16, that is, between the moving tip part 16a and the fixed tip part 16b, can be measured.

On the surface of the main body 11, actuator terminals 21 for applying an electric current to the comb-drive actuator 17, sensor terminals 22 for detecting capacitance variation of the displacement sensor 18, and arm member terminals 23 for impressing AC voltage between the tip parts 16 on tips of the pair of arm members 15 are provided.

As illustrated in FIG. 2, the present embodiment employs a solution containing device 30 as well as the nano-tweezers 10. The solution containing device 30 includes a pair of plate members 31, with a form of plane board each, and a micro chamber 32 formed between the plate members 31. The plate members 31 consist of a top plate member 31a on the upside and a bottom plate member 31b on the downside, and the top plate member 31a and the bottom plate member 31b are configured in parallel allowing a micro gap (for example, a gap of about 300 [μm]) between them. At least, the top plate member 31a is made preferably from transparent material, such as glass. In the micro chamber 32, a solution including DNA is injected and contained. Even though the micro chamber 32 is open in its front (Left side in FIG. 2), the solution contained therein would hardly spill out or evaporate, since the gap between the top plate member 31a and the bottom plate member 31b is microscopic.

The nano-tweezers 10 is attached onto a plane top surface of a tweezers holding device 41, which is fixed onto the top surface of a base member 40 fixed on a laboratory floor etc. so that the surface of the main body 11 becomes horizontal. Thereby, the arm members 15 are made level.

The solution containing device 30 is attached to a solution holding device 42, which is fixed onto the top surface of the base member 40 and is opposing to the tweezers holding device 41. The solution holding device 42 includes a movable holding bed 42a, which can move toward and away from the tweezers holding device 41. And the solution containing device 30 is attached on a flat top surface of the movable holding bed 42a so that the plate members 31 are made level. The position in height of the movable holding bed 42a is adjusted so that the position in height of the micro chamber 32 between the plate members 31 corresponds to that of the arm members 15 of the nano-tweezers 10 attached to the tweezers holding device 41.

Accordingly, when the movable holding bed 42a horizontally moves as shown by a two-directional arrow in FIG. 2 (a), the tip parts 16 of arm members 15 of the nano-tweezers 10 relatively go into and out from the micro chamber 32 of the solution containing device 30, so that the tip parts 16 can be immersed into the solution in the micro chamber 32 as shown in FIG. 2 (b).

FIG. 3 is a photograph showing a positional relationship between the nano-tweezers 10 and the solution containing device 30 the present inventors have really produced, and shows a situation where the tip parts 16 of arm members 15 of the nano-tweezers 10 is just taken out from the micro chamber 32 of the solution containing device 30.

Next will be described a method of detecting DNA, which is a method according to the present embodiment and is a method employed actually by the present inventors to detect DNA with the devices shown in FIG. 3. First a method of bridging a gap between the tip parts 16 with DNA will be described.

Figure 4A:
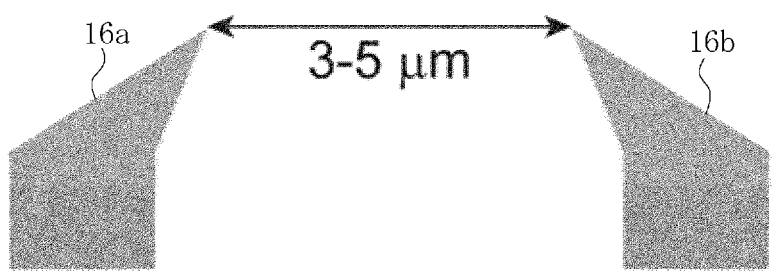
FIG. 4 is a set of views showing a method for fixing primer on the tips of arm members of the nano-tweezers according to the first embodiment of the present invention.
Figure 4B:
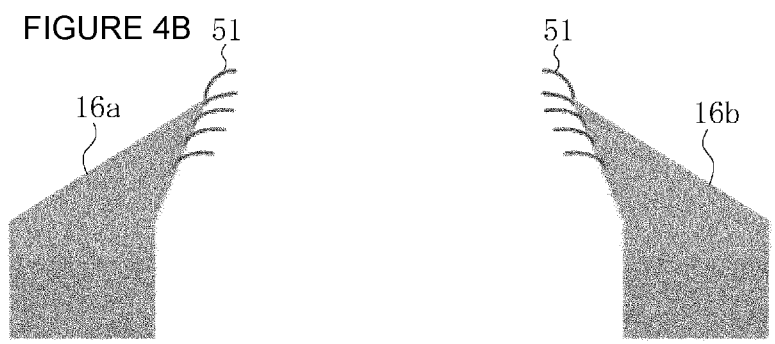
Figure 5A:
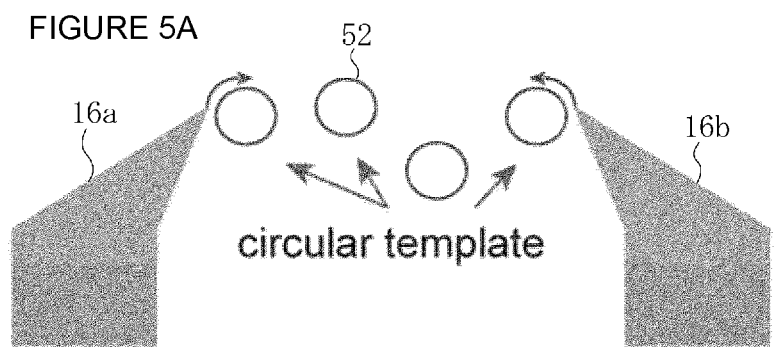
FIG. 5 is a set of views showing a method for generating DNA product on the tips of arm members of the nano-tweezers according to the first embodiment of the present invention.
Figure 5B:
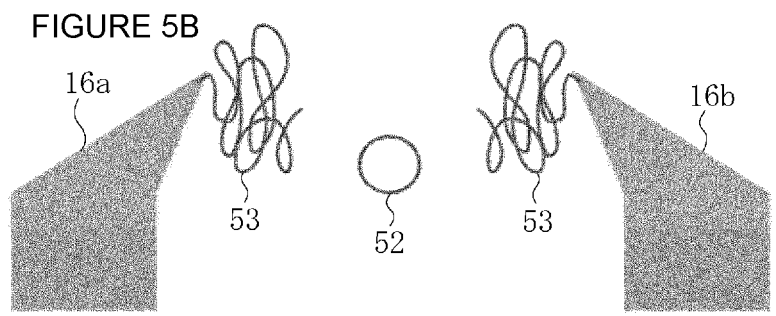

FIG. 4 is a set of views showing a method for fixing primer on the tips of arm members of the nano-tweezers according to the first embodiment of the present invention. FIG. 5 is a set of views showing a method for generating DNA product on the tips of arm members of the nano-tweezers according to the first embodiment of the present invention. FIG. 6 is a set of views showing a DNA bridging between the tips of arm members of the nano-tweezers according to the first embodiment of the present invention. FIG. 7 is a microscopic photo showing the DNA bridging between the tips of arm members of the nano-tweezers according to the first embodiment of the present invention. In FIGS. 4 and 5, (a) and (b) show a first and a second process of the method, in FIG. 6, (a) shows the DNA bridging between the tips, and (b)-(d) show DNA molecules included in the DNA bridge.

As illustrated in FIG. 4 (a), a gap between the opposing tip parts 16 is, at least, about 3-5 [nm]. It is impossible at present to make the gap narrower, since there is a limit to a micromachining technology. Even though the moving tip part 16a is positioned left and the fixed tip part 16b is positioned right in FIGS. 4-6, either of the moving tip part 16a and the fixed tip part 16b may be positioned left or right. The surfaces of the tip parts 16 are coated with gold.

The movable holding bed 42a is moved to the left in FIG. 2 (a), and the tip parts 16 are inserted into the micro chamber 32 of the solution containing device 30 and are immersed into a first solution in the micro chamber 32. Thereby, primer 51 is attached and immobilized on the surfaces of the tip parts 16, as illustrated in FIG. 4 (b). The first solution is a solution including the primer 51.

The present inventors have employed 5'-thiol-modified RCA primer as the primer 51.

Then, the movable holding bed 42a is moved to the right in FIG. 2 (a), and the tip parts 16 are pulled out from the micro chamber 32 of the solution containing device 30. After that, the first solution in the micro chamber 32 is replaced by a different second solution. Again the movable holding bed 42a is moved to the left in FIG. 2 (a), and the tip parts 16 are inserted into the micro chamber 32 of the solution containing device 30 and are immersed into the second solution in the micro chamber 32. The second solution is a solution including circular templates 52 of single stranded DNA.

The present inventors have employed synthesized and circularized oligonucleotide templates as the circular templates 52.

Then, annealing of the circular templates 52 is processed isothermally in a situation where the tip parts 16 are being immersed in the second solution, as illustrated in FIG. 5 (a). The annealing does not need any thermal cycle and can be processed at room temperature. Further, single stranded DNA products 53 are generated utilizing RCA in situ, in a situation where the tip parts 16 are being immersed in the second solution, as illustrated in FIG. 5 (b). The RCA is an effective method of amplifying DNA, which does not need any thermal cycle and can be processed isothermally at room temperature, and its resulting amplification rate can reach up to a billion-fold within an hour.

The present inventors have processed the RCA at 30 [° C.] for two hours and have created extremely long (over 100 [kB], for example) single stranded DNA products 53.

Then, with impressing a designated voltage between the tip parts 16, DNA molecules expand and build a bridge between the tip parts 16, and it's a resulting DNA bridge 54 is generated, as illustrated in FIG. 6 (a). The DNA bridge 54 includes a plurality of single stranded DNA molecules and the DNA is in bundle. Also, DNA of the DNA bridge 54 may be in a bundle including double stranded DNA molecules.

The present inventors have generated a strong electrical field by applying AC voltage with a high frequency (for example, 1 [MHz], 1 [MV/m]) between the tip parts 16 to expand DNA molecules, to mobilize them by DEP (Dielectrophoresis), and to attract them toward the tip parts 16 in left and right, so that the DNA bridge 54 has been generated. An extremely long DNA bridge 54 of more than 15 [μm] in length has been generated as the bridge of DNA with its both ends immobilized on the tip parts 16 in left and right. FIG. 7 is a photograph showing the DNA bridge 54 actually generated in a situation where the gap between the tip parts 16 in left and right was 6 [μm] and the tip parts 16 were outside the micro chamber 32 of the solution containing device 30.

The nano-tweezers 10 can be employed for characterizing DNA bridging between the tip parts 16. The characterization is pursued on real time based on mechanical characteristics or electrical characteristics of DNA.

Specifically, after the DNA bridge 54 was generated, the movable holding bed 42a is moved to the right in FIG. 2 (a), and, when the tip parts 16 are pulled out from the second solution in the micro chamber 32 of the solution containing device 30, the comb-drive actuator 17 of the nano-tweezers 10 is operated to vary the gap between the moving tip part 16a and the fixed tip part 16b at a prescribed frequency and to vibrate the DNA bridging between the tip parts 16. Thereby, the DNA is characterized by measuring its resonance frequency.

For example, when strands of DNA are bonded each other by cross-linking 55 as illustrated in FIG. 6 (b)-(d), the resonance frequency of DNA is thought to vary according to ways of bonding or linking. Therefore, based on the resonance frequencies beforehand measured of the DNA without cross-linking 55 and of the DNA with cross-linking 55 in specific ways, it can be distinguished what way of bonding or linking the DNA in the DNA bridge 54 has. Specifically, since the resonance frequencies are different each other in case where single stranded DNA molecules are bonded by cross-linking 55 in an intrastrand way as illustrated in FIG. 6 (b), in case where single stranded DNA molecules are bonded by cross-linking 55 in an interstrand way as illustrated in FIG. 6 (c), and in case where double stranded DNA molecules are bonded by cross-linking 55 in both an intrastrand way and an interstrand way as illustrated in FIG. 6 (d), it can be distinguished which one of those illustrated in FIG. 6 (b)-(d) dose meet the case.

The DNA is also characterized by measuring its variation of electrical conductivity of the DNA bridging between the tip parts 16, based on varying voltage and current applied between the tip parts 16 of the nano-tweezers 10. And generation of the DNA bridge 54 or existence of DNA molecule can be detected without employing any marker or labeling substances, such as fluorescent reagents, since the electrical conductivity between the tip parts 16 is different before and after the tip parts 16 is bridged by DNA or the DNA bridge 54 is generated.

Next will be described results of characterizing DNA done by the present inventors. First a result of characterizing DNA based on its mechanical characteristics will be described.

Figure 8:
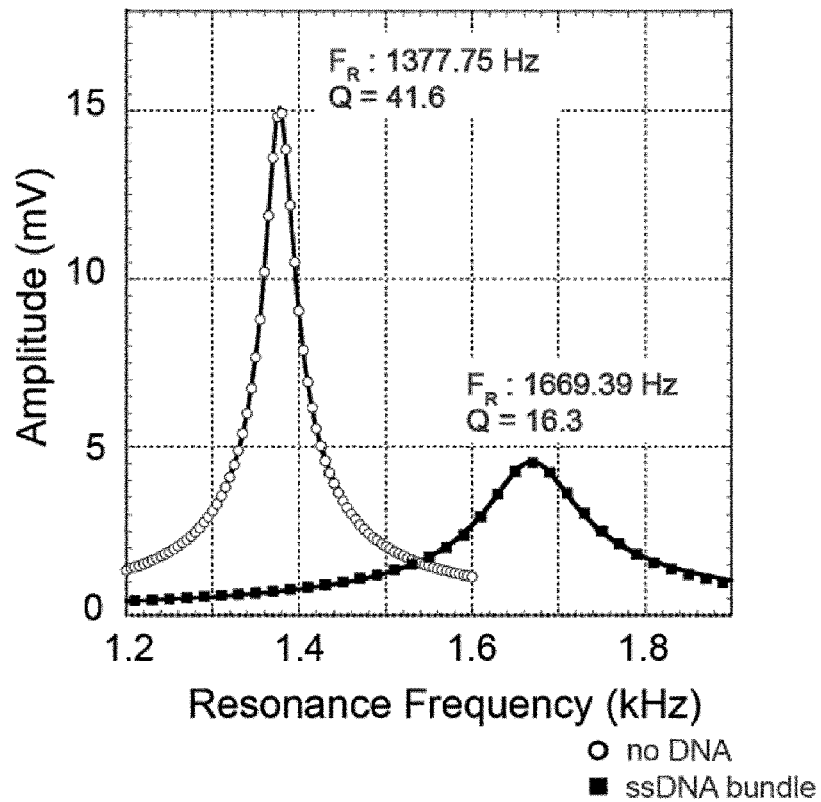
FIG. 8 is a graph showing a resonance frequency shift of the DNA bridging between the tips of arm members of the nano-tweezers according to the first embodiment of the present invention.
Figure 9:
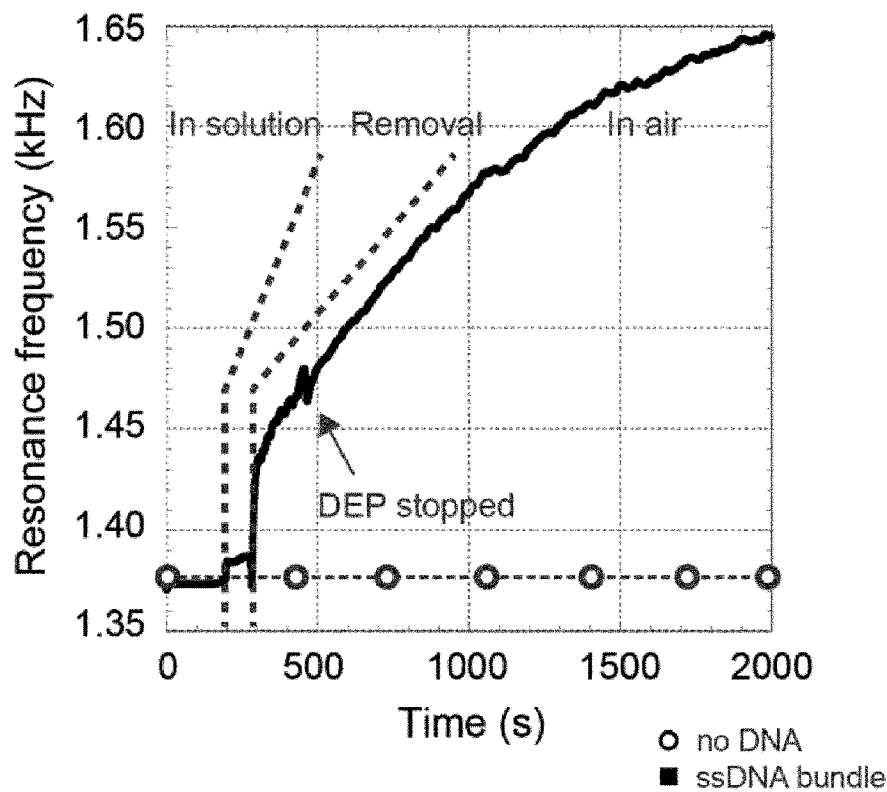
FIG. 9 is a graph showing a time variation of resonance frequency of the DNA bridging between the tips of arm members of the nano-tweezers according to the first embodiment of the present invention.

FIG. 8 is a graph showing a resonance frequency shift of the DNA bridging between the tips of arm members of the nano-tweezers according to the first embodiment of the present invention. FIG. 9 is a graph showing a time variation of resonance frequency of the DNA bridging between the tips of arm members of the nano-tweezers according to the first embodiment of the present invention.

The resonance frequency of the arm members 15, whose tip parts 16 are thought to be connected by the DNA bridge 54 through the above described method, is measured and the measured resonance frequency is compared with that of the initialized arm members 15, whose tip parts 16 are clean with nothing attached thereon as shown in FIG. 4 (a). Thereby, it can be proved in situ whether the DNA bridge 54 between tip parts 16 is really generated or not. That is, DNA can be detected in situ.

FIG. 8 illustrates measurement results of resonance frequency of the arm members 15 processed with employing the nano-tweezers 10 the present inventors have really produced. The present inventors operated the comb-drive actuator 17 of the nano-tweezers 10, varied the frequency of vibration of gap distance between the tip parts 16 of the arm members 15, and measured the amplitude of vibration at each frequency. In FIG. 8, ○ shows a measured value of the situation without DNA or the initial situation where nothing is attached on the tip parts 16, and ■ shows a measured value of the situation of ss DNA bundle or the situation where the DNA bridge 54 with single stranded DNA molecules in a bundle is generated between the tip parts 16. In FIG. 8, the horizontal axis indicates resonance frequency [kHz] and the vertical axis indicates amplitude of vibration [mV].

As FIG. 8 illustrates, the value of resonance frequency is 1669.39 [Hz] in the situation where the DNA bridge 54 with single stranded DNA molecules in a bundle is generated between the tip parts 16, while that is 1377.75 [Hz] in the initial situation where nothing is attached on the tip parts 16.

Therefore, it can be proved in situ whether the DNA bridge 54 between tip parts 16 is really generated or not, through measuring the resonance frequency of the arm members 15 whose tip parts 16 are thought to be connected by the DNA bridge 54, and through referring to FIG. 8.

It has been confirmed that the mechanical characteristics of DNA varies in course of time during and after the process of generating the DNA bridge 54 between the tip parts 16 through the above described method.

FIG. 9 illustrates a time variation of the resonance frequency of the DNA bridge 54 measured with employing the nano-tweezers 10 the present inventors have really produced. In FIG. 9, ○ shows a measured value of the situation without DNA or the initial situation where nothing is attached on the tip parts 16, and ■ shows a measured value of the situation of ss DNA bundle or the situation where the DNA bridge 54 with single stranded DNA molecules in a bundle is generated between the tip parts 16. In FIG. 9, the horizontal axis indicates time elapsed [s] and the vertical axis indicates resonance frequency [kHz].

As FIG. 9 illustrates, even in the case where the DNA bridge 54 is generated, until the tip parts 16 are inserted into the micro chamber 32 of the solution containing device 30 and are immersed into a solution in the micro chamber 32, that is, prior to the In solution situation, the value of resonance frequency is the same as of the initial situation since nothing is attached on the parts 16. Then, through the above described method in a situation where the tip parts 16 are immersed into the solution, the DNA bridge 54 is generated with DNA molecules bridging between the tip parts 16, and, thereby, the value of resonance frequency increases. When the tip parts 16 begin to be pulled out from the solution in the micro chamber 32 or when Removal starts, the value of resonance frequency increases considerably. And, even when the tip parts 16 are out from the solution in the micro chamber 32 and DEP comes to a stop or when DEP stopped situation is accomplished, further when the tip parts 16 are completely in the air or when In air situation is accomplished, the value of resonance frequency continues increasing with the elapse of time.

Next will be described a result of characterizing DNA based on its electrical characteristics.

Figure 10:
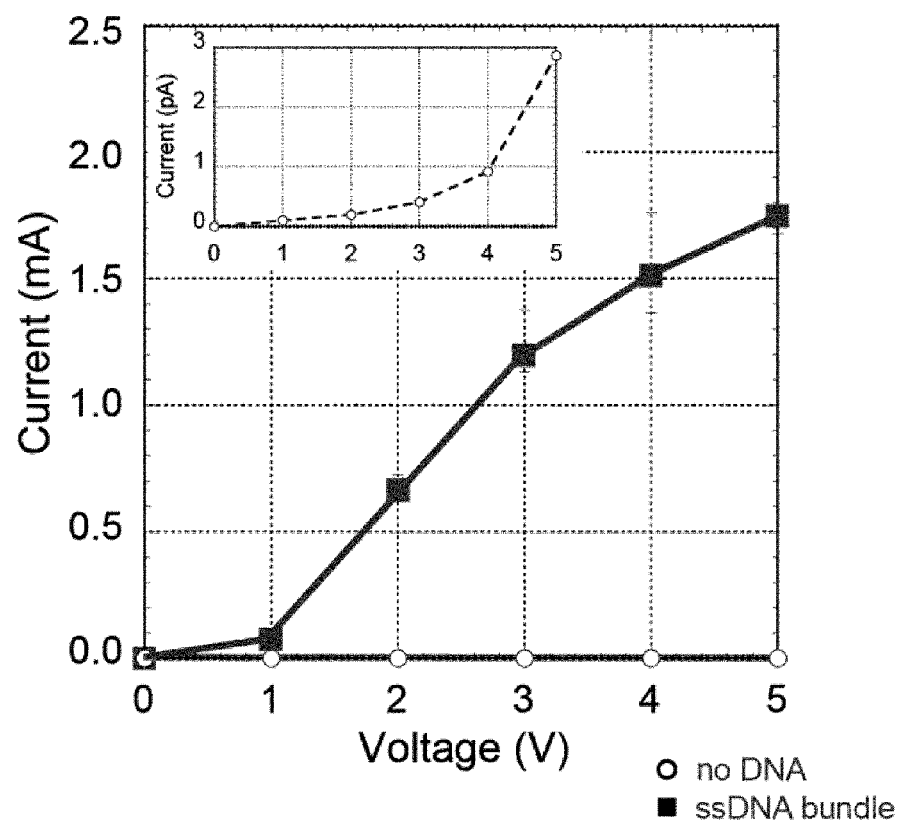
FIG. 10 is a first graph showing an electric conductivity of the DNA bridging between the tips of arm members of the nano-tweezers according to the first embodiment of the present invention.
Figure 11:
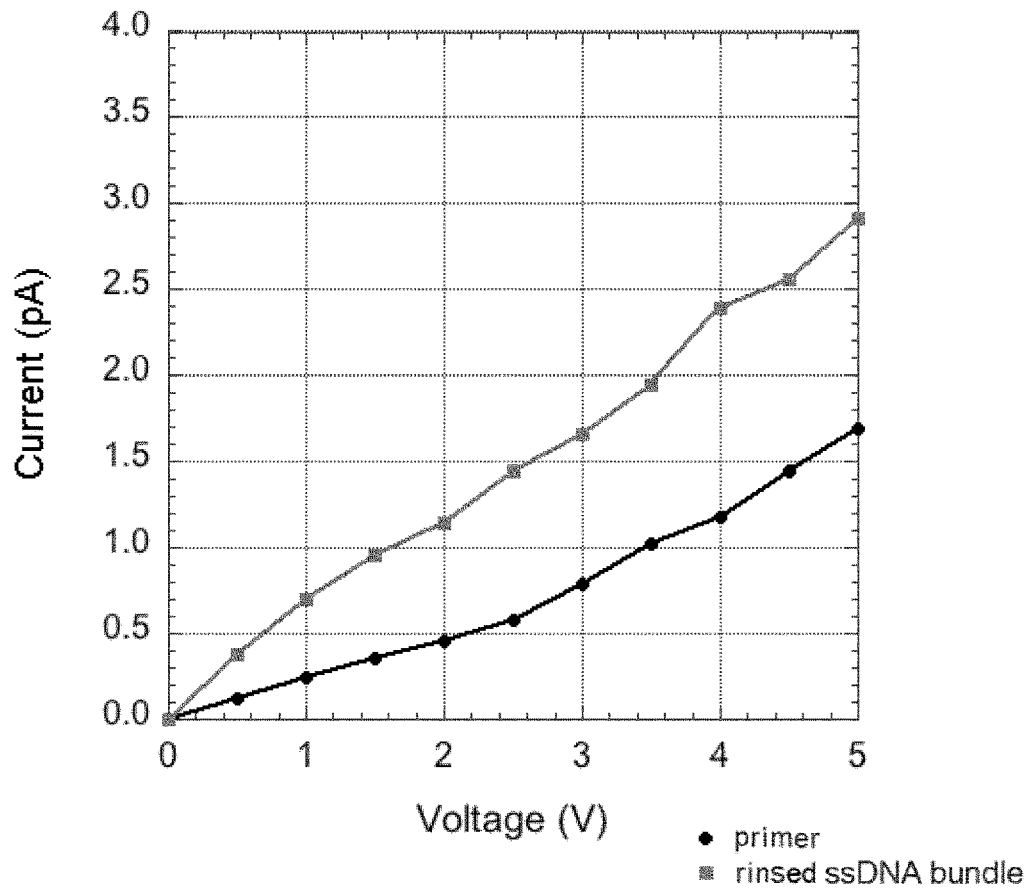
FIG. 11 is a second graph showing an electric conductivity of the DNA bridging between the tips of arm members of the nano-tweezers according to the first embodiment of the present invention.

FIG. 10 is a first graph showing an electric conductivity of the DNA bridging between the tips of arm members of the nano-tweezers according to the first embodiment of the present invention. FIG. 11 is a second graph showing an electric conductivity of the DNA bridging between the tips of arm members of the nano-tweezers according to the first embodiment of the present invention.

Electric current at the time when voltage is applied between the tip parts 16 of the arm members 15, which are thought to be connected by the DNA bridge 54 through the above described method, is measured, and the measured electric current is compared with that at the time when voltage is impressed between the initialized tip parts 16, which are clean with nothing attached thereon as shown in FIG. 4 (*a*). Thereby, it can be proved in situ whether the DNA bridge 54 between tip parts 16 is really generated or not. That is, DNA can be detected in situ.

FIG. 10 illustrates measurement results of electric current at the time when voltage was applied between the tip parts 16, and the measurement was processed with employing the nano-tweezers 10 the present inventors have really produced. The present inventors varied the voltage impressed between the tip parts 16 of the nano-tweezers 10, and measured the value of electric current at each voltage. In FIG. 10, ○ shows a measured value of the situation without DNA or the initial situation where nothing is attached on the tip parts 16, and ■ shows a measured value of the situation of ss DNA bundle or the situation where the DNA bridge 54 with single stranded DNA molecules in a bundle is generated between the tip parts 16. In FIG. 10, the horizontal axis indicates voltage [V] and the vertical axis indicates electric current [mA].

FIG. 10 also shows another graph in a frame, whose scale of vertical axis is expanded with electric current unit [pA] replacing [mA]. Because, in the initial situation where nothing is attached on the tip parts 16, variation of electric current is too little to distinguish when electric current unit of the vertical axis is [mA].

As FIG. 10 illustrates, the value of electric current increase a lot as voltage rises and goes beyond 1.7 [mA] when voltage reached at 5 [V], for example, in the situation where the DNA bridge 54 with single stranded DNA molecules in a bundle is generated between the tip parts 16, while that does not increase so much as voltage rises and does not reach 3 [pA] when voltage reached 5 [V], for example, in the initial situation where nothing is attached on the tip parts 16.

Therefore, it can be proved in situ whether the DNA bridge 54 between tip parts 16 is really generated or not, through measuring the electric current by applying voltage between the tip parts 16, which are thought to be connected by the DNA bridge 54 through the above described method, and through referring to FIG. 10.

By the way, in a point of view to confirm on real time basis that the DNA bridge 54 is completed, it would be desirable to compare with the stage just before the DNA bridge 54 is completed. That is, it would be desirable to compare with the situation where the primer 51 is immobilized on the tip parts 16 as shown in FIG. 4 (*b*), rather than with the initial situation where nothing is attached on the tip parts 16 as shown in FIG. 4 (*a*).

FIG. 11 illustrates another measurement result of electric current at the time when voltage was impressed between the tip parts 16, and the measurement was processed with employing the nano-tweezers 10 the present inventors have really produced. The present inventors varied the voltage applied between the tip parts 16 of the nano-tweezers 10, and measured the value of electric current at each voltage. In FIG. 11, ● shows a measured value of the situation of primer or the situation where 5'-thiol-modified RCA primer as the primer 51 is attached and immobilized on the tip parts 16, and ■ shows a measured value of the situation of rinsed ss DNA bundle or the situation where the DNA bridge 54 with single stranded DNA molecules in a bundle is generated between the tip parts 16 and the DNA bridge 54 is rinsed by being immersed in pure water. In FIG. 11, the horizontal axis indicates voltage [V] and the vertical axis indicates electric current [pA].

As FIGS. 10 and 11 illustrate, the value of electric current increase a lot as voltage rises in the situation where the DNA bridge 54 with single stranded DNA molecules in a bundle is generated between the tip parts 16, while that does not increase so much as voltage rises in the situation where the primer 51 is immobilized on the tip parts 16.

Therefore, it can be proved in situ whether the DNA bridge 54 between tip parts 16 is really generated or not, through measuring the electric current by impressing voltage between the tip parts 16, which are thought to be connected by the DNA bridge 54 through the above described method, and through referring to FIGS. 10 and 11.

As FIG. 10 illustrates, the value of electric current increase a lot as voltage rises in the situation where the DNA bridge 54 has not been rinsed, while, as FIG. 11 illustrates, that does not increase so much as voltage rises in the situation where the DNA bridge 54 has been rinsed by being immersed in pure water. The reason is that, in the situation where the DNA bridge 54 has not been rinsed, a lot of salt is attached to the DNA bridge 54 and, thereby, its electric conductivity is high. By rinsing the DNA bridge 54 through immersing it in pure water, the salt is washed out from it and its own electric conductivity can be measured.

As described above, the present embodiment provides a method of detecting DNA using the nano-tweezers 10 as a detection device having the tip parts 16 of arm members 15 as a couple of electrodes. The method comprising immobilizing a primer 51 on the tip parts 16, making a bridge of DNA expanded between the tip parts 16, by immersing the tip parts 16 in a solution including circular templates 52 of single stranded DNA, annealing the circular templates 52, and generating single stranded DNA product 53 utilizing RCA, with impressing a designated voltage between the tip parts 16, and characterizing the bridge of DNA which includes multiple single stranded DNA molecules between the tip parts 16.

Thereby, DNA can be easily and surely detected without employing any marker or labeling substances, such as fluorescent reagents.

And, at least a part of the tip parts 16 is preferably coated with gold.

Also, making the bridge of DNA expanded between the tip parts 16 is processed isothermally. Therefore, DNA is easily detected, since any thermal manipulation to vary temperature of solutions for amplifying DNA, such as the conventional method of detecting DNA employed, is no more needed.

Further, characterizing the bridge of DNA is based on a resonance frequency of DNA bridging between the tip parts 16, specifically, by varying the gap distance between the tip parts 16 at designated frequencies. Thereby, DNA can be detected in situ.

And, DNA bridging between the tip parts 16 is in a bundle. Further, the DNA is in a bundle including double stranded DNA molecules.

Further, characterizing the bridge of DNA is based on an electrical conductance of DNA bridging between the tip parts 16. Thereby, DNA can be detected in situ.

Further, characterizing the bridge of DNA is made on real time measurement of DNA bridging between the tip parts 16. Thereby, characteristics of DNA varying in course of time can be grasped.

Further, different primers 51 can be immobilized on the opposing tip parts 16 so that a single stranded complementary DNA is generated. The generated single stranded DNA forms a double stranded DNA with each other, since they are complementary.

Further, plural pairs of tip parts 16 are arranged in parallel, for example, in thickness direction and different primers 51 are immobilized thereon, so that amplifying, bridging and characterizing DNA can be proceeded based on templates interacting the primers 51.

Next, a second embodiment of the present invention will now be described. Structural features similar to the first embodiment are denoted by common reference materials, and repeated description of operation and effects similar to those of the first embodiment is omitted.

Figure 12A:
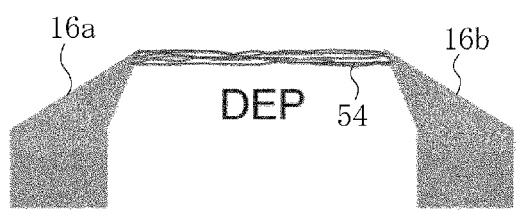
FIG. 12 is a set of views showing a method for coating the DNA bridging between the tips of arm members of the nano-tweezers with gold nanoparticles according to a second embodiment of the present invention.
Figure 12B:
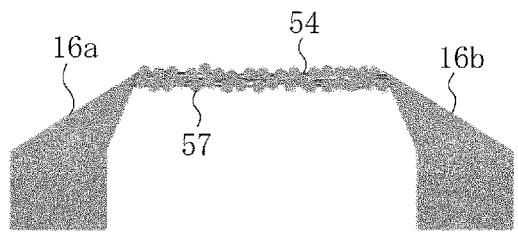

FIG. 12 is a set of views showing a method for coating the DNA bridging between the tips of arm members of the nano-tweezers with gold nanoparticles according to the second embodiment of the present invention. FIG. 13 is a set of microscopic photos showing the state where the DNA bridging between the tips of arm members of the nano-tweezers coated with gold nanoparticles according to the second embodiment of the present invention. FIG. 14 is a graph showing an electric conductivity of the DNA bridging between the tips of arm members of the nano-tweezers coated with palladium nanoparticles according to the second embodiment of the present invention. In FIG. 12, (*a*) shows a view of the DNA bridging between the tips, (*b*) shows a view of the DNA coated with gold nanoparticles, in FIG. 13, (*a*) is a photograph the state of no DNA, (*b*) and (*c*) are photographs of the first and second states of the DNA coated with gold nanoparticles.

In the present embodiment, as illustrated in FIG. 12 (*b*), the DNA bridging between the tip parts 16 of arm members 15 of the nano-tweezers 10 is coated with nanoparticles 57 of gold (Au), so that the existence of DNA bridging between the tip parts 16 is confirmed.

Structures of the nano-tweezers 10 and the solution containing device 30 are similar to the first embodiment, therefore description about them is omitted. Also, description of operation generating the DNA bridge 54, as shown in FIG. 12 (*a*), by building a bridge of DNA between the tip parts 16 of arm members 15 of the nano-tweezers 10 is omitted, since it is similar to the first embodiment. FIG. 12 (*a*) is the same as FIG. 6 (*a*) described in the first embodiment.

After the DNA bridge 54 between the tip parts 16 was generated, as shown in FIG. 12 (*a*), the movable holding bed 42*a* is moved to the right in FIG. 2 (*a*), and the tip parts 16 are pulled out from the micro chamber 32 of the solution containing device 30. After that, the second solution in the micro chamber 32 is replaced by a different third solution. Again the movable holding bed 42*a* is moved to the left in FIG. 2 (*a*), and the tip parts 16 are inserted into the micro chamber 32 of the solution containing device 30 and are immersed into the third solution in the micro chamber 32.

The third solution is a solution including nanoparticles 57 of gold. The nanoparticles 57 are ultrafine particles of 1-100 [nm] in diameter. The third solution includes the nanoparticles 57 at a ratio of, for example, 3-30 [ng/µl].

Thereby, the DNA bridge 54 generated between the tip parts 16 is coated with nanoparticles 57 of gold as shown in FIG. 12 (*b*). The DNA bridge 54 coated with nanoparticles 57 of gold is more visible and is of higher electrical conductance (of lower electrical resistance) than the uncoated DNA bridge 54. Therefore, through taking microscopic photos or through measuring electric current by impressing voltage between the tip parts 16, it can be easily proved that the DNA bridge 54 exists between tip parts 16 or whether the DNA bridge 54 between tip parts 16 is really generated or not.

The present inventors coated the DNA bridge 54 generated between tip parts 16 with nanoparticles 57 of gold, by employing, as the third solution, a couple of solutions including nanoparticles 57 of gold at a ratio of 3 [ng/µl] and at a ratio of 30 [ng/µl] respectively. FIG. 13 is a set of photographs showing the DNA bridges 54 actually generated in a situation where the gap between the left and right tip parts 16 was 6 [µm], and, in FIG. 13, (*a*) shows a situation before generating the DNA bridges 54, (*b*) shows a situation where the DNA bridge 54 is coated with nanoparticles 57 of gold through immersing it in a solution including nanoparticles 57 of gold at a ratio of 3 [ng/µl], and (*c*) shows a situation where the DNA bridge 54 is coated with nanoparticles 57 of gold through immersing it in a solution including nanoparticles 57 of gold at a ratio of 30 [ng/µl]. The gap between the left and right tip parts 16 was 6 [µm], as shown in FIG. 13 (*a*).

As FIG. 13 (*b*) shows, the DNA bridge 54 coated with nanoparticles 57 of gold is easy to be distinguished. Comparison between FIG. 13 (*b*) and FIG. 13 (*c*) illustrates that the DNA bridge 54 immersed in a solution including more nanoparticles 57 of gold is easier to be distinguished since it is coated with more nanoparticles 57 of gold.

As results of measuring electric currents by impressing voltage between the tip parts 16 and calculating electrical resistances between the tip parts 16, the calculated electrical resistances were 26 [TΩ] in case of FIG. 13 (*a*), 692 [GΩ] in case of FIG. 13 (*b*), and 390 [GΩ] in case of FIG. 13 (*c*), respectively.

This illustrates that the DNA bridge 54 coated with nanoparticles 57 of gold, in comparison with the uncoated DNA bridge 54, has an order of magnitude lower electrical resistance and is easier to be detected. It also illustrates that the more nanoparticles 57 of gold coat the DNA bridge 54, the more electrical resistance decreases and the more the DNA bridge 54 is detected easily.

The material of nanoparticles 57 for coating DNA is not necessarily limited to gold but can be any other electric conductive material, such as palladium (Pd).

The present inventors coated the DNA bridge 54 generated between the tip parts 16 with nanoparticles 57 of palladium, by employing, as the third solution, a solution including nanoparticles 57 of palladium. FIG. 14 illustrates measurement results of electric current at the time when voltage was impressed between the tip parts 16, and the measurement was processed with employing the nano-tweezers 10 the present inventors have really produced. The present inventors varied the voltage impressed between the tip parts 16 of the nano-tweezers 10, and measured the value of electric current at each voltage. FIG. 14 shows a measured value of the situation of ss DNA bundle or the situation where the DNA bridge 54 with single stranded DNA molecules in a bundle is generated between the tip parts 16, a measured value of the situation of DNA coated with Pd or the situation where the DNA bridge 54 generated between the tip parts 16 is coated with nanoparticles 57 of palladium, and a measured value of the situation of rinsed DNA coated with Pd or the situation where the DNA bridge 54 generated between the tip parts 16 is coated with nanoparticles 57 of palladium and the DNA bridge 54 coated with nanoparticles 57 of palladium has been rinsed by being immersed in pure water. In FIG. 14, the horizontal axis indicates voltage [V] and the vertical axis indicates electric current [pA].

As FIG. 14 illustrates, the value of electric current increase a lot as voltage rises in the situation where the DNA bridge 54 is coated with nanoparticles 57 of palladium, while that does not increase so much as voltage rises in the situation where the DNA bridge 54 with single stranded DNA molecules in a bundle is generated between the tip parts 16. In the situation after rinsing the DNA bridge 54, the electric conductivity is low, since the salt has been washed out from it.

As described above, the present embodiment provides a method of detecting DNA using the nano-tweezers 10 as a detection device having the tip parts 16 of arm members 15 as a couple of electrodes. The method comprising immobilizing a primer 51 on the tip parts 16, making a bridge of the DNA expanded between the tip parts 16, by immersing the tip parts 16 in a solution including circular templates 52 of the single stranded DNA, annealing the circular templates 52, and generating single stranded DNA product 53 utilizing RCA, with impressing a designated voltage between the electrodes; coating the bridge of the DNA with conductive nanoparticles 57, and verifying existence of the bridge of DNA between the tip parts 16.

Thereby, existence of DNA bridging between the tip parts 16 can be easily and surely proved.

Next, a third embodiment of the present invention will be described. Structural features similar to the first and second embodiments are denoted by common reference materials, and repeated description of operation and effects similar to those of the first and second embodiments is omitted.

Figure 15:
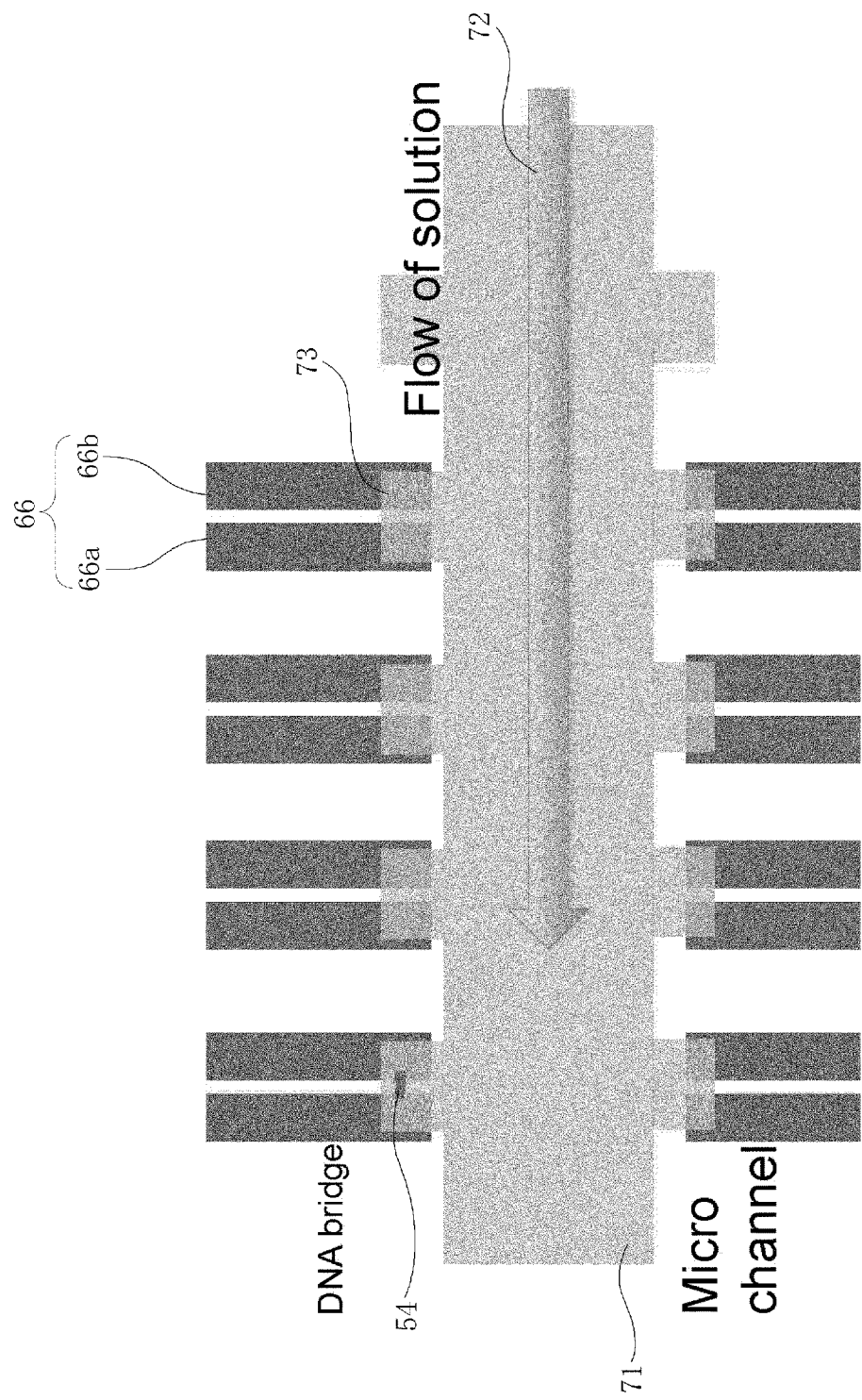
FIG. 15 is a schematic diagram showing a micro fluid device according to a third embodiment of the present invention.
Figure 17A:
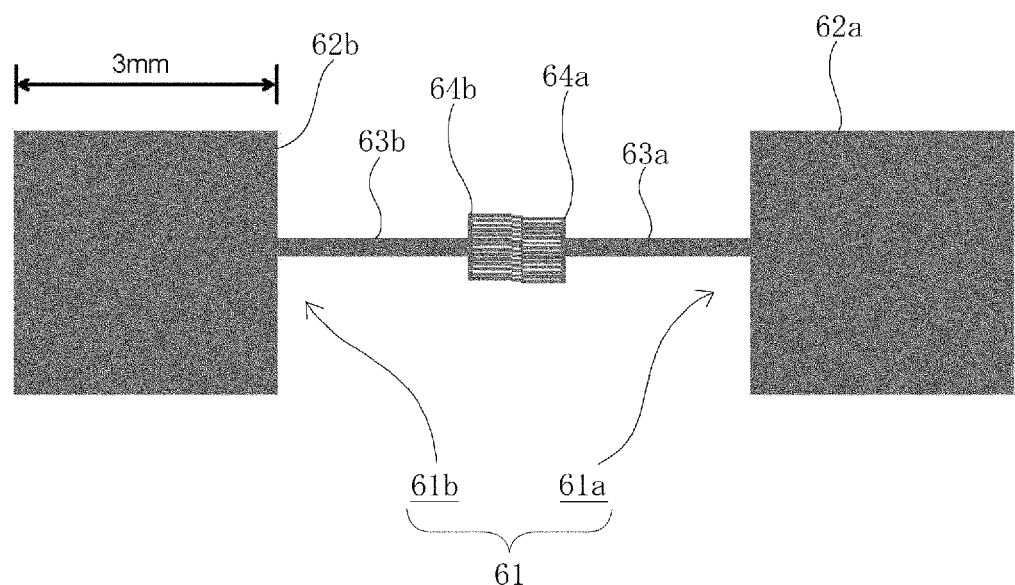
FIG. 17 is a set of views showing an electrode unit of the micro fluid device according to the third embodiment of the present invention.
Figure 17B:
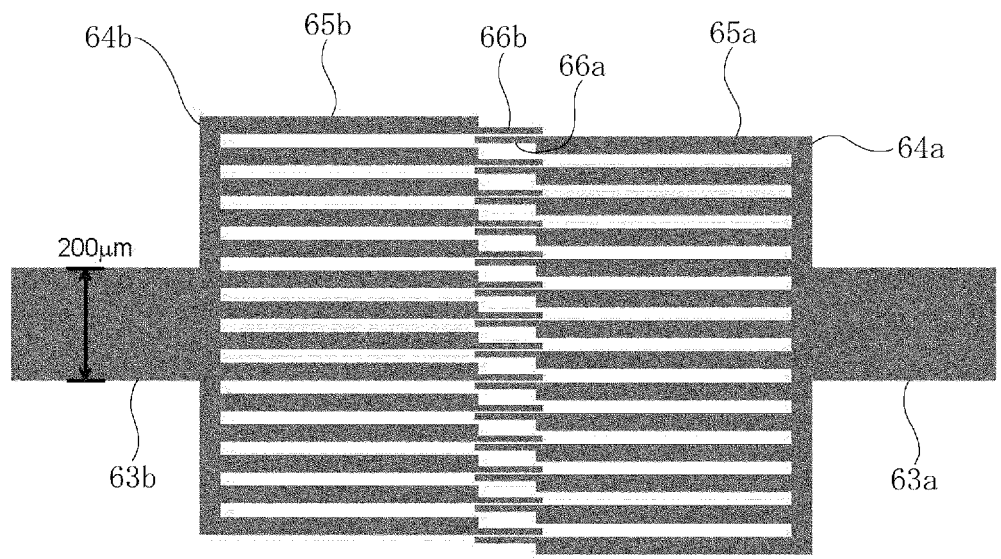
Figure 18A:
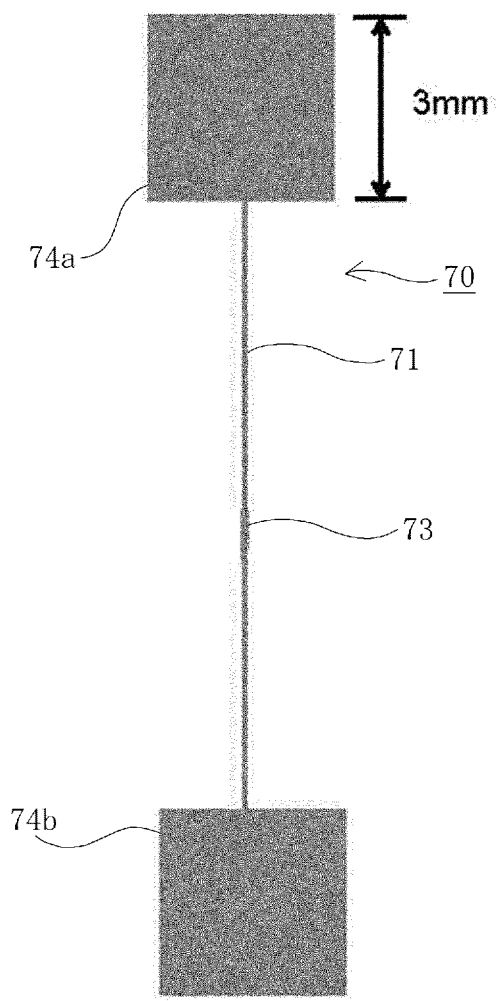
FIG. 18 is a set of views showing a micro channel unit of the micro fluid device according to the third embodiment of the present invention.
Figure 18B:
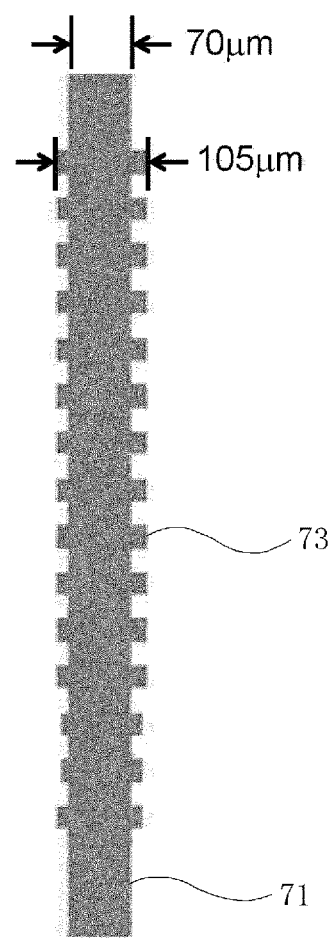
Figure 19B:
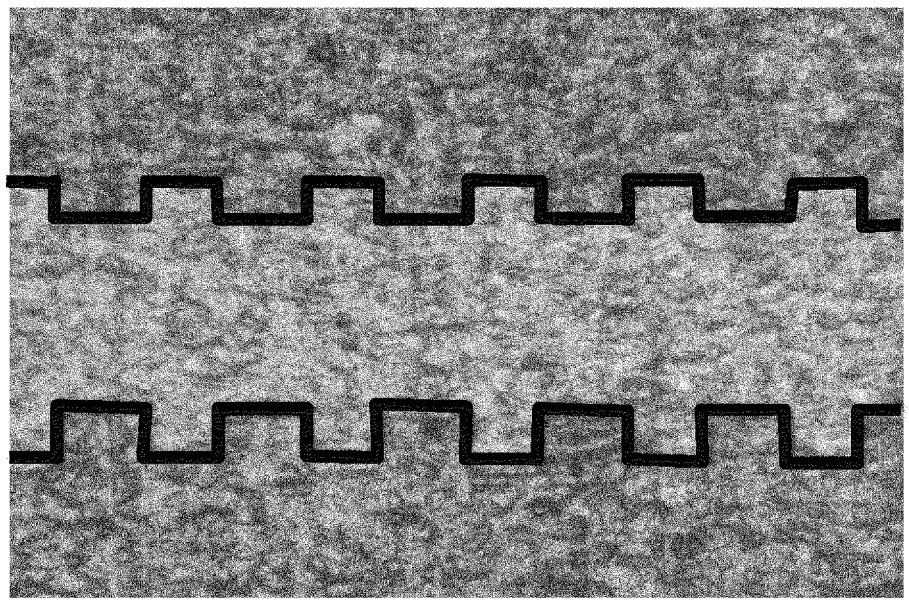
FIG. 19 is a set of microscopic photos showing projection structures of the micro channel unit of the micro fluid device according to the third embodiment of the present invention.
Figure 19A:
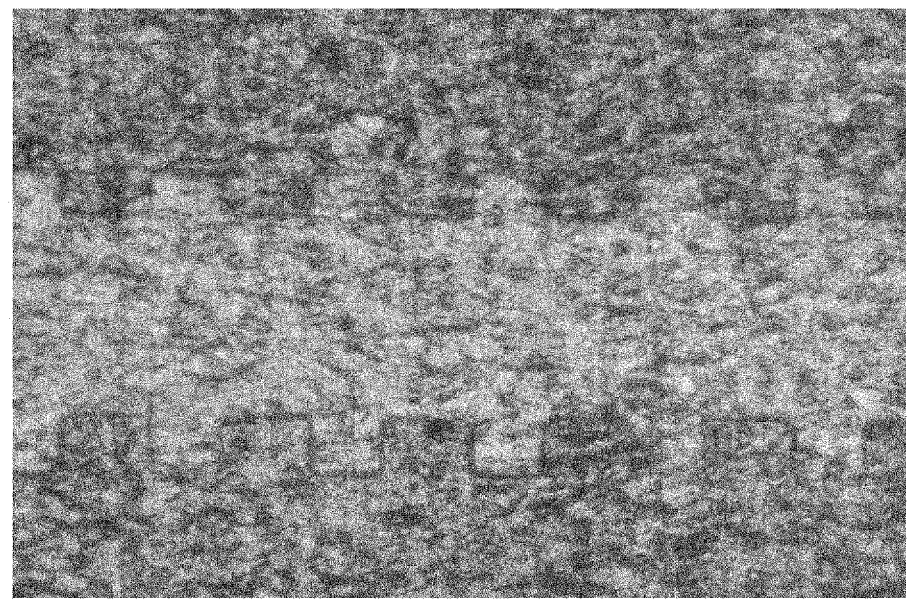
Figure 20B:
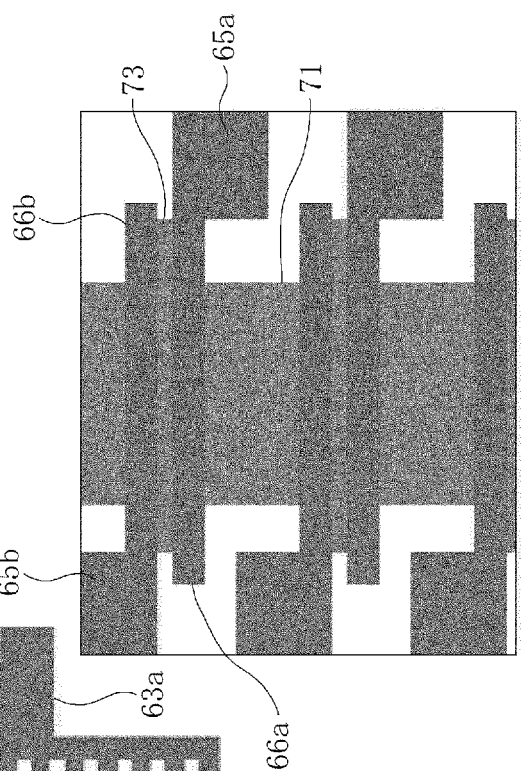
FIG. 20 is a set of views showing a DNA capturing portion of the micro fluid device according to the third embodiment of the present invention.
Figure 20A:
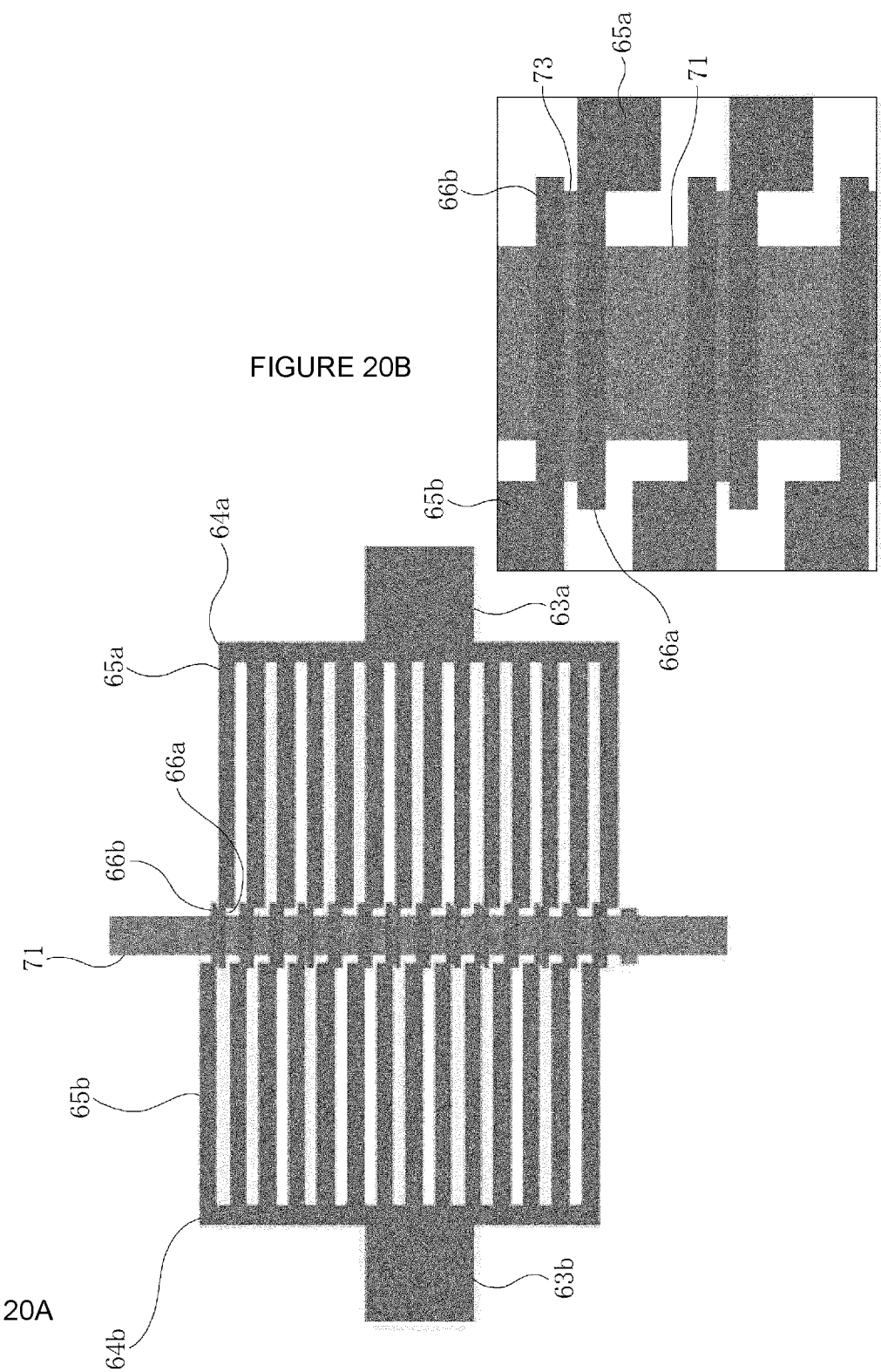

FIG. 15 is a schematic diagram showing a micro fluid device according to the third embodiment of the present invention. FIG. 16 is a set of photos showing the micro fluid device according to the third embodiment of the present invention. FIG. 17 is a set of views showing an electrode unit of the micro fluid device according to the third embodiment of the present invention. FIG. 18 is a set of views showing a micro channel unit of the micro fluid device according to the third embodiment of the present invention. FIG. 19 is a set of microscopic photos showing projection structures of the micro channel unit of the micro fluid device according to the third embodiment of the present invention. FIG. 20 is a set of views showing a DNA capturing portion of the micro fluid device according to the third embodiment of the present invention. FIG. 21 is a set of microscopic photos showing the DNA capturing portion of the micro fluid device according to the third embodiment of the present invention. In FIG. 16, (a) shows a whole structure of the micro fluid device, (b) shows the electrode unit, (c) shows electrode tip parts, in FIG. 17, (a) shows a whole structure of the electrode unit, (b) shows an enlarged central part of the electrode unit, in FIG. 18, (a) shows a whole structure of the micro channel unit, (b) shows an enlarged central part of the micro channel unit, in FIG. 19, (a) is a microscopic photo showing projection structures, (b) is a microscopic photo including black bordering lines added to the photo of (a), in FIG. 20, (a) shows a whole structure of the DNA capturing portion, (b) shows an enlarged central part of the DNA capturing portion, in FIG. 21, (a) is a photo showing a state of no DNA, (b) is a photo showing a state of captured DNA with fluorescent labels.

The present embodiment employs a micro fluid device as illustrated in FIG. 16 (a) for detecting DNA. The micro fluid device includes an electrode unit 61 as illustrated in FIG. 17 and a micro channel unit 70, as illustrated in FIG. 18, which is integrated with the electrode unit 61. More specifically, the micro fluid device includes a cover slip with the electrode unit 61 of gold (Au) patterned on its one side, and polymer sheet with the micro channel unit 70 embedded therein, which is laid on the cover slip. In the example illustrated in FIG. 16 (a), the cover slip is a transparent and rectangular glass plate 26 [mm] in length and 36 [mm] in width.

The electrode unit 61 includes a pair of a first electrode unit 61a and a second electrode unit 61b, which are the same in shape. As illustrated in FIG. 17, the first electrode unit 61a and the second electrode unit 61b are arranged to face each other, so that the electrode unit 61 has a symmetrical shape as a whole.

The first electrode unit 61a and the second electrode unit 61b respectively have a first and a second connection pads 62a, 62b, a first and a second axial parts 63a, 63b whose base ends are connected to the first and the second connection pads 62a, 62b, a first and a second comb parts 64a, 64b which are connected to the tip ends of the first and the second axial parts 63a, 63b, a plurality of first and second teeth parts 65a, 65b included in the first and the second comb parts 64a, 64b, and first and second electrode tip parts 66a, 66b each of which extrudes from each of the first and the second teeth parts 65a, 65b.

Figure 16A:
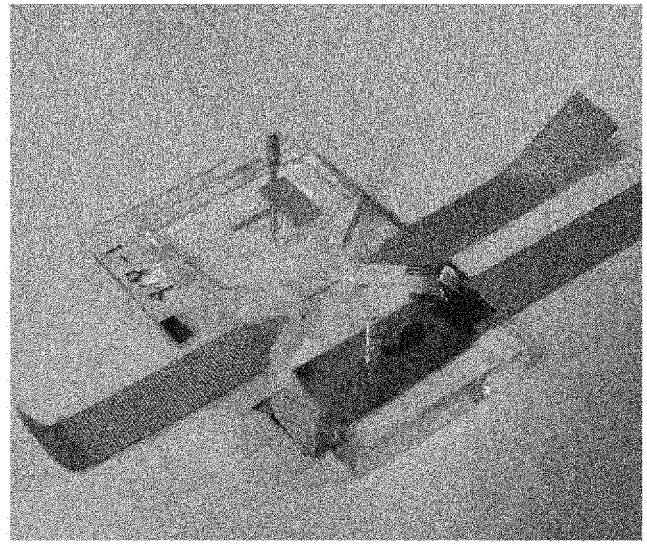
FIG. 16 is a set of photos showing the micro fluid device according to the third embodiment of the present invention.
Figure 16B:
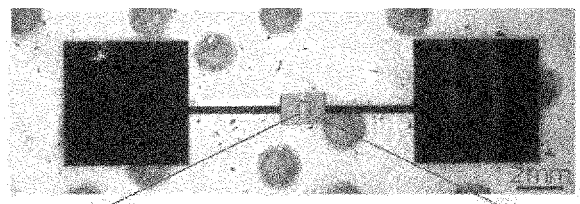

The first and the second connection pads 62a, 62b are square portions 3 [mm] in length and width, and are connected to tip ends of tape like conductive lines whose other ends are connected to an outer source of electrical power, as illustrated in FIG. 16(a). The first and the second axial parts 63a, 63b are band like portions 200 [μm] in width. The first and the second teeth parts 65a, 65b are straight and narrow band like portions, and the first and the second electrode tip parts 66a, 66b are straight band like portions narrower than the first and the second teeth parts 65a, 65b.

Figure 16C:
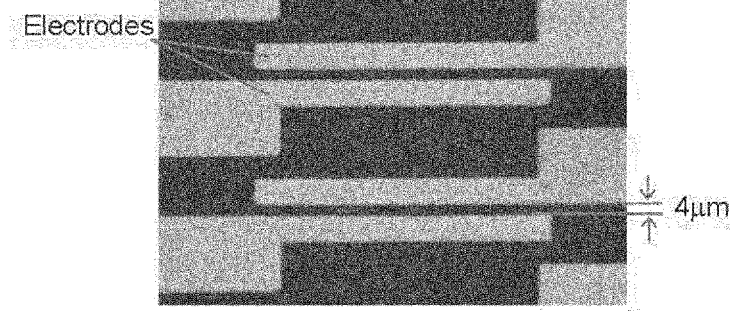

The corresponding pairs of the first and the second teeth parts 65a, 65b are arranged in parallel with each other, and the corresponding pairs of the first and the second electrode tip parts 66a, 66b are arranged in parallel with each other. A distance between the first and the second electrode tip parts 66a, 66b in a corresponding pair is 4 [μm], as illustrated in FIG. 16(c).

The micro channel unit 70 includes, as illustrated in FIG. 18, a first and a second connection portion 74a, 74b, a straight micro channel 71 connecting the first and the second connection portion 74a, 74b, and a plurality of projection structures 73 which are formed into extrusions from both the side edges of the micro channel 71 in its center portion.

The first and the second connection portion 74a, 74b are square portions 3 [mm] in length and width, and are connected, via pipe like metals, to tip ends of tubes whose other ends are connected to an outer fluid providing source and an outer fluid sink, as illustrated in FIG. 16(a). The micro channel 71 is a flow pass for solutions, such as the first, second, third solutions, etc. and pure water, that is, fluid to flow, and a straight band like portion 70 [μm] in width and 3 [μm] in thickness (depth). The projection structures 73 are portions formed into extrusions from both the side edges of the micro channel 71 and formed into a symmetrical shape, and the distance between the tips of a pair of the projection structures 73 opposed each other is 150 [μm]. Each of the projection structures 73 is filled with fluid flowing in the micro channel 71 since it is a hollow communicating with the micro channel 71.

The electrode unit 61 and the micro channel 71 are combined in a manner illustrated in FIG. 20, specifically in such a manner that the extending direction of the first and the second teeth parts 65a, 65b and the first and the second electrode tip parts 66a, 66b is at right angles to that of the micro channel 71, that the micro channel 71 lies between the corresponding tips of the first and the second teeth parts 65a, 65b, and that, at least partially, a pair of the first and the second electrode tip parts 66a, 66b overlaps a pair of the projection structures 73.

In the micro fluid device with the electrode unit 61 and the micro channel unit 70 combined as above described, a DNA bridge 54 may be generated between the first and the second electrode tip parts 66a, 66b corresponding each other, by applying a predetermined voltage to the electrode unit 61 with making the solution flow through the micro channel 71 in a direction indicated by an arrow 72, as illustrated in FIG. 15.

Since the solution flows in the micro channel 71, even when the DNA bridge 54 is generated between the first and the second electrode tip parts 66a, 66b corresponding each other, the DNA bridge 54 might be removed from the first and the second electrode tip parts 66a, 66b and driven away by the flow of solution. However, the DNA bridge 54 generated between the first and the second electrode tip parts 66a, 66b in a location corresponding to one of the projection structures 73 is not driven away, as illustrated in FIG. 15, since the solution is stagnant in the projection structures 73.

The solutions or fluids, in which the first and the second electrode tip parts 66a, 66b are immersed, may be easily exchanged just by replacing the solution flowing in the micro channel 71 with others, for example, replacing the first solution with the second solution or with pure water for rinsing.

By employing the micro fluid device as above described, the gap between the first and the second electrode tip parts 66a, 66b may be bridged by DNA through the same method as those of the first and the second embodiments.

Figure 21A:
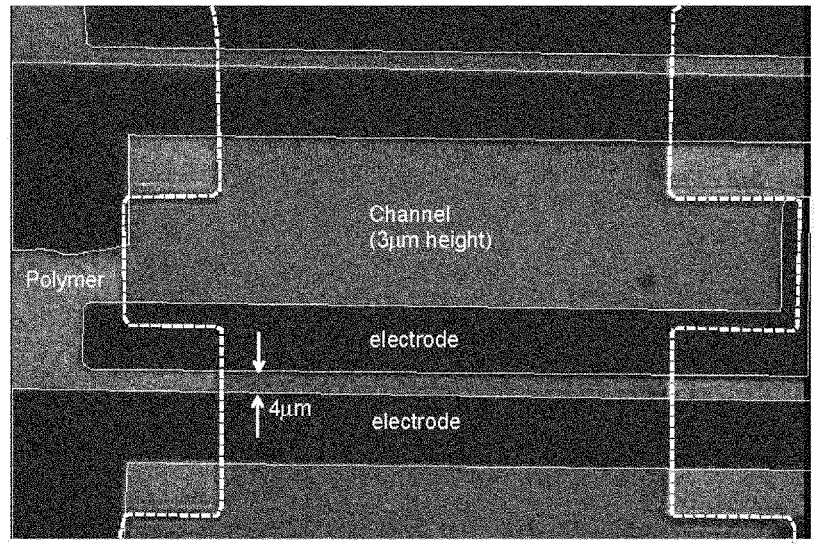
FIG. 21 is a set of microscopic photos showing the DNA capturing portion of the micro fluid device according to the third embodiment of the present invention.
Figure 21B:
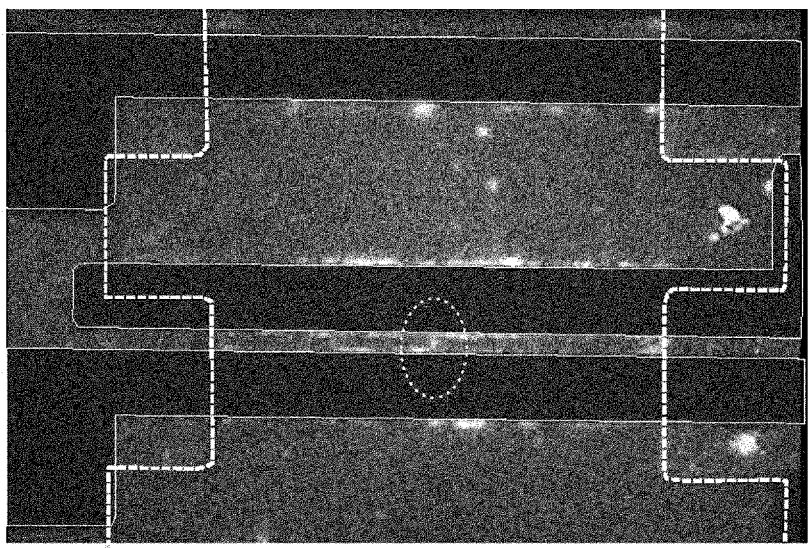

The present inventors have confirmed a fact that the gap between the first and the second electrode tip parts 66a, 66b is possible to be bridged by DNA through a preliminary experiment actually employing the micro fluid device. In the preliminary experiment, any amplification of DNA has not been processed. And, in the micro fluid device employed in the preliminary experiment, the combination of the electrode unit 61 and the micro channel unit 70 was imperfect so that a pair of the first and the second electrode tip parts 66a, 66b did not overlap accurately a pair of the projection structures 73, as illustrated in FIG. 21(a). Further, in the preliminary experiment, the existence of a bridge of DNA expanded between the first and the second electrode tip parts 66a, 66b was confirmed through labeling DNA with fluorescent dye called YOYO-1 and through fluorescent observation, for convenience, as illustrated in a dotted ellipse in FIG. 21(b).

As described above, the present embodiment provides a method of detecting DNA using the micro fluid device combining the electrode unit 61 having a pair of the first and the second electrode tip parts 66a, 66b as a pair of electrodes and the micro channel unit 70. And, through the same method as those of the first and the second embodiments, it is possible to make the bridge of DNA expanded between a pair of the first and the second electrode tip parts 66a, 66b, to characterize the DNA and to confirm the existence of the DNA.

Thereby, DNA can be easily and surely detected.

As described in the first through third embodiments, the present invention relates to a method of detecting DNA whereby DNA is easily and surely detected. Therefore, the present invention can be applied wide-ranging fields, from label free detection of mutations and pathogens without employing any marker or labeling substances such as fluorescent reagents, genotyping to physical characterization of sequence specific DNA in response to various DNA interaction agents (e.g. cross-linking chemicals) and physical effects such as irradiation. Physical characterization of sequence specific DNA will find direct applications in translational research (e.g. cancer drugs functional validation) and environmental tests. The present invention permits both DNA detection and physical analysis with one platform.

The present invention is not limited to the above embodiments, but may be diversely modified and varied. Thus, the modifications and variations are not excluded from the scope of protection of the present invention.

INDUSTRIAL APPLICABILITY

The present invention is applicable to a method of detecting DNA.

REFERENCE SIGNS LIST

10: Nano-tweezers
16: Tip
51: Primer
52: Circular template
53: Single stranded DNA product
57: Nanoparticle

The invention claimed is:

1. A method of detecting DNA using a detection device with at least a couple of electrodes separated by a gap, the method comprising:
   (a) immobilizing a primer on a tip of each of the at least a couple of electrodes;
   (b) immersing the tip of the electrodes in a solution comprising single stranded DNA circular templates;
   (c) annealing the single stranded DNA circular templates to the immobilized primer on the tip of each of the at least a couple of electrodes;
   (d) amplifying the single stranded DNA circular templates to produce single stranded DNA molecules on the tip of each of the at least a couple of electrodes utilizing rolling circle amplification (RCA);
   (e) applying a determined voltage between the electrodes so as to expand, within the gap, the single stranded DNA molecules that were amplified on either electrode toward the other electrode, said single stranded DNA molecules connecting the tip of the other electrode, thereby building a DNA bridge between the tips of the electrodes; and
   (f) characterizing the DNA bridge based on a resonance frequency of said DNA bridge and/or based on an electrical conductance of said DNA bridge.

2. The method of detecting DNA according to claim 1, wherein at least a part of the tip of the electrodes is coated with gold.

3. The method of detecting DNA according to claim 1, wherein making the DNA bridge expanded between the electrodes is processed isothermally.

4. The method of detecting DNA according to claim 1, wherein a gap between each of the at least a couple of electrodes is varied at designated frequencies.

5. The method of detecting DNA according to claim 1, wherein the single stranded DNA molecules expanded between the electrodes are in a bundle.

6. The method of detecting DNA according to claim 5, wherein the bundle comprises double stranded DNA molecules formed from the single stranded DNA molecules.

7. The method of detecting DNA according to claim 1, wherein characterizing the DNA bridge is made on real time measurement of the DNA bridge between the electrodes.

8. The method of detecting DNA according to claim 1, further comprising immobilizing different primers on the tip of opposite electrodes so that single stranded complementary DNA molecules are generated.

9. The method of detecting DNA according to claim 1, further comprising immobilizing different primers on the tip of multiple couples of electrodes to make multiple DNA bridges and characterize each of the DNA bridges.

10. A method of detecting DNA using a detection device with at least a couple of electrodes separated by a gap, the method comprising:
  (a) immobilizing a primer on a tip of each of the electrodes;
  (b) immersing the tip of the electrodes in a solution comprising single stranded DNA circular templates;
  (c) annealing the single stranded DNA circular templates to the immobilized primer on the tip of each of the electrodes;
  (d) amplifying the single stranded DNA circular templates to produce single stranded DNA molecules on the tip of each of the electrodes utilizing rolling circle amplification (RCA);
  (e) applying a determined voltage between the electrodes so as to expand, within the gap, the single stranded DNA molecules that were amplified on either electrode, said single stranded DNA molecules connecting the tip of the other electrode, thereby building a DNA bridge between the electrodes;
  (f) coating the DNA bridge with conductive nanoparticles; and
  (g) verifying building of the DNA bridge between the electrodes based on a resonance frequency of said DNA bridge and/or based on an electrical conductance of said DNA bridge.

11. The method of detecting DNA according to claim 10, further comprising immobilizing different primers on the tip of multiple couples of electrodes to make multiple DNA bridges and verify each of the DNA bridges.

12. The method of detecting DNA according to claim 1, wherein a plurality of primers are immobilized on the tip of the electrodes.

13. The method of detecting DNA according to claim 10, wherein a plurality of primers are immobilized on the tip of the electrodes.

* * * * *